US011155853B2

(12) United States Patent
Bouriakov et al.

(10) Patent No.: US 11,155,853 B2
(45) Date of Patent: *Oct. 26, 2021

(54) SYSTEM AND METHOD FOR TARGETED DEPLETION OF NUCLEIC ACIDS

(71) Applicant: Roche Sequencing Solutions, Inc., Pleasanton, CA (US)

(72) Inventors: Venera Bouriakov, Madison, WI (US); Daniel Burgess, Black Earth, WI (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/592,432

(22) Filed: Oct. 3, 2019

(65) Prior Publication Data
US 2020/0024646 A1 Jan. 23, 2020

Related U.S. Application Data

(63) Continuation of application No. 15/423,850, filed on Feb. 3, 2017, now Pat. No. 10,472,666.

(60) Provisional application No. 62/295,307, filed on Feb. 15, 2016.

(51) Int. Cl.
*C12Q 1/6806* (2018.01)
*C12N 9/22* (2006.01)

(52) U.S. Cl.
CPC ............ *C12Q 1/6806* (2013.01); *C12N 9/22* (2013.01); *C12Y 301/26004* (2013.01)

(58) Field of Classification Search
CPC . C12Q 1/6806; C12N 9/22; C12Y 301/26004
See application file for complete search history.

(56) References Cited

U.S. PATENT DOCUMENTS

| | | | |
|---|---|---|---|
| 6,040,138 A | 3/2000 | Lockhart et al. |
| 6,613,516 B1 | 9/2003 | Christians |
| 7,645,578 B2 | 1/2010 | Wang |
| 9,005,891 B2 | 4/2015 | Dominick |
| 2005/0003369 A1 | 1/2005 | Christians et al. |
| 2007/0009913 A1 | 1/2007 | Wang |
| 2008/0102454 A1 | 5/2008 | Wang |
| 2009/0203085 A1 | 8/2009 | Kurn et al. |
| 2011/0111409 A1 | 5/2011 | Sinicropi |

FOREIGN PATENT DOCUMENTS

| | | |
|---|---|---|
| WO | 2009/055732 A1 | 4/2009 |
| WO | 2014/165814 A1 | 10/2014 |

OTHER PUBLICATIONS

Wu, K. Et Al., Globin Reduction Protocol: A Method for Processing Whole Blood RNA Samples for Improved Array Results, Affymetrix Technical Note, (2003), pp. 1-9, vol. Rev. 2.

*Primary Examiner* — Joseph G. Dauner
(74) *Attorney, Agent, or Firm* — Eric Grant Lee; Daniel Agnew

(57) ABSTRACT

The present disclosure provides a system and method for depleting target nucleic acids from a nucleic acid sample. In one aspect, a kit according to the present disclosure includes a plurality of DNA probes. Each of the DNA probes is hybridizable to form a heteroduplex with at least one of a plurality of target RNA transcripts in a nucleic acid sample. The number of unique target RNA transcripts hybridized by the plurality of DNA probes is at least three. The kit further includes an enzyme having RNA-DNA hybrid ribonucleotidohydrolase activity, where degrades at least the RNA portion of the heteroduplex.

14 Claims, 9 Drawing Sheets

Specification includes a Sequence Listing.

SEQUENCE LISTING

<160> NUMBER OF SEQ ID NOS: 243

<210> SEQ ID NO 1
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 1
ctggttgagc acagggtact ttattgatgg tacatgac         38

<210> SEQ ID NO 2
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 2
ggtgcggctc cctaggcccc tcccctcttc aaggggtc         38

<210> SEQ ID NO 3
<211> LENGTH: 38
<212> TYPE: DNA

```
<213> ORGANISM: Artificial Sequence
<220> FEATURE:
<223> OTHER INFORMATION: DNA probe sequence for depletion of target RNA

<400> SEQUENCE: 3
catggcaact gtgaggaggg gagattcagt gtggtggg                              38

<210> SEQ ID NO 4
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 4
actgagtgtg gcagggactc cccagcagtg agggtctc                              38

<210> SEQ ID NO 5
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 5
tcttcctctt gtgctcttgc tggggctggt ggtccagg                              38

<210> SEQ ID NO 6
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 6
tcttactcct tggaggccat gtgggccatg aggtccac                              38

<210> SEQ ID NO 7
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 7
ccctgttgct gtagccaaat tcgttgtcat accaggaa                              38

<210> SEQ ID NO 8
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 8
gagcttgaca aagtggtcgt tgagggcaat gccagccc                              38

<210> SEQ ID NO 9
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 9
gcgtcaaagg tggaggagtg ggtgtcgctg ttgaagtc                              38
```

<210> SEQ ID NO 10
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 10
aggagaccac ctggtgctca gtgtagccca ggatgccc                              38

<210> SEQ ID NO 11
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 11 gaggggccc tccgacgcct gcttccaccac cttcttga                              38

<210> SEQ ID NO 12
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 12
tcatcatatt tggcaggttt ttctagacgg caggtcag                              38

<210> SEQ ID NO 13
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 13
ccaccactga cacgttggca gtggggacac ggaaggcc                              38

<210> SEQ ID NO 14
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 14
gccagtgagc ttcccgttca gctcagggat gaccttgc                              38

<210> SEQ ID NO 15
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 15
acagccttgg cagcgccagt agaggcaggg atgatgtt                              38

<210> SEQ ID NO 16
<211> LENGTH: 38
<212> TYPE: DNA
<213> ORGANISM: Artificial Sequence
<220> FEATURE:

<223> OTHER INFORMATION: DNA probe sequence for depletion of target RNA

<400> SEQUENCE: 16
ggagagcccc gcggccatca cgccacagtt tcccggag                                    38

<210> SEQ ID NO 17
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 17
gccatccaca gtcttctggg tggcagtgat ggcatgga                                    38

<210> SEQ ID NO 18
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 18
gtggtcatga gtccttccac gataccaaag ttgtcatg                                    38

<210> SEQ ID NO 19
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 19
tgaccttggc cagggtgct aagcagttgg tggtgcag                                     38

<210> SEQ ID NO 20
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 20
ggcattgctg atgatcttga ggctgttgtc atacttct                                    38

<210> SEQ ID NO 21
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 21
tggttcacac ccatgacgaa catgggggca tcagcaga                                    38

<210> SEQ ID NO 22
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 22
gggcagagat gatgaccctt ttggctcccc cctgcaaa                                    38

```
<210> SEQ ID NO 23
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 23
agccccagcc ttctccatgg tggtgaagac gccagtgg                           38

<210> SEQ ID NO 24
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 24
tccacgacgt actcagcgcc agcatcgccc cacttgat                           38

<210> SEQ ID NO 25
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 25
tggagggatc tcgctcctgg aagatggtga tgggattt                           38

<210> SEQ ID NO 26
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 26
attgatgaca agcttcccgt tctcagcctt gacggtgc                           38

<210> SEQ ID NO 27
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 27
tggaatttgc catgggtgga atcatattgg aacatgta                           38

<210> SEQ ID NO 28
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 28
ccatgtagtt gaggtcaatg aaggggtcat tgatggca                           38

<210> SEQ ID NO 29
<211> LENGTH: 38
<212> TYPE: DNA
<213> ORGANISM: Artificial Sequence
<220> FEATURE:
<223> OTHER INFORMATION: DNA probe sequence for depletion of target RNA
```

<400> SEQUENCE: 29
aatatccact ttaccagagt taaaagcagc cctggtga					38

<210> SEQ ID NO 30
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 30
aggcgcccaa tacgaccaaa tccgttgact ccgacctt					38

<210> SEQ ID NO 31
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 31
ccttccccat ggtgtctgag cgatgtggct cggcccgc					38

<210> SEQ ID NO 32
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 32
cggcgcgaac acatccggcc tgcgcccgcc cctgccgc					38

<210> SEQ ID NO 33
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 33
tcaggccgtc cctagcctcc cgggtttctc tccgcccg					38

<210> SEQ ID NO 34
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 34
ttcacctggc gacgcaaaag aagatgcggc tgactgtc					38

<210> SEQ ID NO 35
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 35
acaggaggag cagagagcga agcgggaggc tgcgggct					38

<210> SEQ ID NO 36
<211> LENGTH: 38

```
<212> TYPE: DNA
<213> ORGANISM: Artificial Sequence
<220> FEATURE:
<223> OTHER INFORMATION: DNA probe sequence for depletion of target RNA

<400> SEQUENCE: 36
atttatagaa accgggggcg cggcggcagg cggtgact                              38

<210> SEQ ID NO 37
<211> LENGTH: 38
<212> TYPE: DNA
<213> ORGANISM: Artificial Sequence
<220> FEATURE:
<223> OTHER INFORMATION: DNA probe sequence for depletion of target RNA

<400> SEQUENCE: 37
gaccccgcct cccgccaggc tcagccagtc ccagccca                              38

<210> SEQ ID NO 38
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 38
ggtctggagc tcgtcggact cagagggcct gtctt                                 35

<210> SEQ ID NO 39
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 39
cacaatgttc ttgaagaagt ggactacggg gtttt                                 35

<210> SEQ ID NO 40
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 40
cagtcctctc ccctttccct gcgacggggg tggtg                                 35

<210> SEQ ID NO 41
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 41
tcctggtctc tggccttcgg ccccccagct aaatc                                 35

<210> SEQ ID NO 42
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 42
```
cttgtgagcc gatttatagt cggacgctct gcctc                                35

<210> SEQ ID NO 43
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 43
aaaaattttg gaaagcgtgc cctgggcatc gactc                                35

<210> SEQ ID NO 44
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 44
tctagccatg ggtgatccag agcgactatc tcttc                                35

<210> SEQ ID NO 45
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 45
taagaagctg aggacaggat tccggaacca ggtgg                                35

<210> SEQ ID NO 46
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 46
taggtaacag gggcaagtgg gattaaagtt ttaag                                35

<210> SEQ ID NO 47
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 47
gtgcacaact ccgcaggcat taggggaggg gtcat                                35

<210> SEQ ID NO 48
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 48
ttggccggaa attgccggta ggctgccgtg gcctg                                35

<210> SEQ ID NO 49
<211> LENGTH: 35
<212> TYPE: DNA
<213> ORGANISM: Artificial Sequence

```
<220> FEATURE:
<223> OTHER INFORMATION: DNA probe sequence for depletion of target RNA

<400> SEQUENCE: 49
catcacatcc aggctctcgg aggtggctgc actgt                                 35

<210> SEQ ID NO 50
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 50
gggacagttt taaccgtttt ctgttttcat gttct                                 35

<210> SEQ ID NO 51
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 51
ctgggggcac attgcggggg aaggaacgtg atctt                                 35

<210> SEQ ID NO 52
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 52
tggagggacg tctgtgcacc tggcccctg aagac                                  35

<210> SEQ ID NO 53
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 53
ccgcagccac ggcgaaaaga aagtccaagg gtgga                                 35

<210> SEQ ID NO 54
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 54
cagctgtgtg cctccatggc agtgaccagc aaaag                                 35

<210> SEQ ID NO 55
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 55
ggatgtcaac agtcctctct gccgcccacg tcctc                                 35
```

<210> SEQ ID NO 56
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 56
tttaggaggt gagagaagga caggaaaaaa aaaca                         35

<210> SEQ ID NO 57
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 57
gccactcctt gactgtctaa tcctgttagg aaaaa                         35

<210> SEQ ID NO 58
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 58
tgcccagccc gcatgtcaca taccaaaagc tccca                         35

<210> SEQ ID NO 59
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 59
gaggtggccc cctctctgtg ctgccccacg ttgga                         35

<210> SEQ ID NO 60
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 60
caggtacttg gatccgtgcc tctgggaggg tctct                         35

<210> SEQ ID NO 61
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 61
acgcgaattc agctaattgg ggtgtgtggg cagcc                         35

<210> SEQ ID NO 62
<211> LENGTH: 35
<212> TYPE: DNA
<213> ORGANISM: Artificial Sequence
<220> FEATURE:
<223> OTHER INFORMATION: DNA probe sequence for depletion of target RNA -continued

<400> SEQUENCE: 62
gccattgccc agcccacgtt tgcctccttt tcctc                               35

<210> SEQ ID NO 63
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 63
atctccatca ccaaatctcc aggaagaccc tgttt                               35

<210> SEQ ID NO 64
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 64
ccaccatgca gggcaacggt gacgtccaga ggcca                               35

<210> SEQ ID NO 65
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 65
ggctgtggtt tggaaacgag gttgttcata gaggc                               35

<210> SEQ ID NO 66
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 66
ccttctgctc tgagtgcgca agtcttcctg gactc                               35

<210> SEQ ID NO 67
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 67
tatgggcgac tggcgcggct gcgaggctgt ctaga                               35

<210> SEQ ID NO 68
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 68
cactgtgcac tgccgctgcc agcacgcccg gtcac                               35

<210> SEQ ID NO 69

```
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 69
gaagtgaatg agccggttat cttctcaggg agggt                              35

<210> SEQ ID NO 70
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 70
caggtgcacg cctgtgccta ctcgctacca cgcgt                              35

<210> SEQ ID NO 71
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 71
tgggaggaag ccatgcctgg catggtccat ggtac                              35

<210> SEQ ID NO 72
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 72
ggggccgtct gctcagcccg tgtgtctcgg tgagt                              35

<210> SEQ ID NO 73
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 73
gtgttaagaa ggatatggtc agaagagctc tttgt                              35

<210> SEQ ID NO 74
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 74
gggtcagtag gttagggagg gaggcgcgaa aggag                              35

<210> SEQ ID NO 75
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 75
```
tctttggaag gcctatcaat cacaggtgcg ctaaa              35

<210> SEQ ID NO 76
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 76
tactcctcat ctccgtcctc ggggagggtg atgcc              35

<210> SEQ ID NO 77
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 77
gaattagaat tggattaaga agacgcgttt tggca              35

<210> SEQ ID NO 78
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 78
gctatatatt aatagacatg gtattaagcc cacac              35

<210> SEQ ID NO 79
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 79
gtttgtgtct ggagttttgt tctttgtaac tctct              35

<210> SEQ ID NO 80
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 80
acctcagctc agcgacgcag agtgcttctg ctgaa              35

<210> SEQ ID NO 81
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 81
cagcacgtgc tgtgtgggtg cggccacgta tggat              35

<210> SEQ ID NO 82
<211> LENGTH: 35
<212> TYPE: DNA

```
<213> ORGANISM: Artificial Sequence
<220> FEATURE:
<223> OTHER INFORMATION: DNA probe sequence for depletion of target RNA

<400> SEQUENCE: 82
aaagaagcgc ccgatggagt caaggatgcc cgtgt                              35

<210> SEQ ID NO 83
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 83
ttcaatattc aggaacagtg tacactttcc gttca                              35

<210> SEQ ID NO 84
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 84
gggtaccttg ccagagcccc gcttgggcgc acccc                              35

<210> SEQ ID NO 85
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 85
gctgcgggca tgagagggca gagggctccg gcccg                              35

<210> SEQ ID NO 86
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 86
tgccgggtgg tgtgagtcct tgtacatgtt gcaca                              35

<210> SEQ ID NO 87
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 87
ccggccgtgt gacttctggg gcagggagcc gtagt                              35

<210> SEQ ID NO 88
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 88
aatgtctttg tggtttgtag agaatagtca acggt                              35
```

<210> SEQ ID NO 89
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 89
taaggagaag atggttaggt ctacggaggc tccag                          35

<210> SEQ ID NO 90
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 90
gatgaaattg atggcccta agatagagga gacac                           35

<210> SEQ ID NO 91
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 91
ttggtattgg gttatggcag ggggttttat attga                          35

<210> SEQ ID NO 92
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 92
aagtaggact gctgtgatta ggacggatca gacga                          35

<210> SEQ ID NO 93
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 93
tagtagtata gtgatgccag cagctaggac tggga                          35

<210> SEQ ID NO 94
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 94
tcctccggcg gggtcgaaga aggtggtgtt gaggt                          35

<210> SEQ ID NO 95
<211> LENGTH: 35
<212> TYPE: DNA
<213> ORGANISM: Artificial Sequence
<220> FEATURE:

```
<223> OTHER INFORMATION: DNA probe sequence for depletion of target RNA

<400> SEQUENCE: 95
gtgaccgaaa aatcagaata ggtgttggta tagaa                                      35

<210> SEQ ID NO 96
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 96
ggagattatt ccgaagcctg gtaggataag aatat                                      35

<210> SEQ ID NO 97
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 97
gtatccaaat ggttcttttt ttccggagta gtaag                                      35

<210> SEQ ID NO 98
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 98
aaaccctagg aagccaattg atatcatagc tcaga                                      35

<210> SEQ ID NO 99
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 99
gcctaggact ccagctcatg cgccgaataa taggt                                      35

<210> SEQ ID NO 100
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 100
gtctacgtct attcctactg taaatatatg gtgtg                                      35

<210> SEQ ID NO 101
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 101
ggggatagcg atgattatgg tagcggaggt gaaat                                      35
```

```
<210> SEQ ID NO 102
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 102
gcttccgtgg agtgtggcga gtcagctaaa tactt                              35

<210> SEQ ID NO 103
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 103
gatgaatcct agggctcaga gcactgcagc agatc                              35

<210> SEQ ID NO 104
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 104
gtttgctaat acaatgccag tcaggccacc tacgg                              35

<210> SEQ ID NO 105
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 105
ggctacaacg tagtacgtgt cgtgtagtac gatgt                              35

<210> SEQ ID NO 106
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 106
tatgatggca aatacagctc ctattgatag gacat                              35

<210> SEQ ID NO 107
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 107
tagggtgtag cctgagaata ggggaaatca gtgaa                              35

<210> SEQ ID NO 108
<211> LENGTH: 35
<212> TYPE: DNA
<213> ORGANISM: Artificial Sequence
<220> FEATURE:
<223> OTHER INFORMATION: DNA probe sequence for depletion of target RNA
```

<400> SEQUENCE: 108
gccgatgaat atgatagtga aatggatttt ggcgt          35

<210> SEQ ID NO 109
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 109
tccggatagg ccgagaaagt gttgtgggaa gaaag          35

<210> SEQ ID NO 110
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 110
gcctggctgg cccagctcgg ctcgaataag gaggc          35

<210> SEQ ID NO 111
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 111
tcatgtggtg tatgcatcgg ggtagtccga gtaac          35

<210> SEQ ID NO 112
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 112
tactgctgtt agagaaatga atgagcctac agatg          35

<210> SEQ ID NO 113
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 113
tcgcttcgaa gcgaaggctt ctcaaatcat gaaaa          35

<210> SEQ ID NO 114
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 114
tagtcactcc aggtttatgg agggttcttc tacta          35

<210> SEQ ID NO 115
<211> LENGTH: 35

```
<212> TYPE: DNA
<213> ORGANISM: Artificial Sequence
<220> FEATURE:
<223> OTHER INFORMATION: DNA probe sequence for depletion of target RNA

<400> SEQUENCE: 115
gtatacgggt tcttcgaatg tgtggtaggg tgggg                          35

<210> SEQ ID NO 116
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 116
ggctgtgacg ataacgttgt agatgtggtc gttac                          35

<210> SEQ ID NO 117
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 117
gattatgatg ggtattacta tgaagaagat tatta                          35

<210> SEQ ID NO 118
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 118
gggggcaccg attattaggg gaactagtca gttgc                          35

<210> SEQ ID NO 119
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 119
taagagtcag aagcttatgt tgtttatgcg gggaa                          35

<210> SEQ ID NO 120
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 120
ggcctccact atagcagatg cgagcaggag tagga                          35

<210> SEQ ID NO 121
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 121
```

```
gttccctgct aagggagggt agactgttca acctg                                35
```

<210> SEQ ID NO 122
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 122

```
agggaagta gcgtcttgta gacctacttg cgctg                                 35
```

<210> SEQ ID NO 123
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 123

```
aatgggggct tcaatcggga gtactactcg attgt                                35
```

<210> SEQ ID NO 124
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 124

```
gacagctcat gagtgcaaga cgtcttgtga tgtaa                                35
```

<210> SEQ ID NO 125
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 125

```
gtttagacgt ccgggaattg catctgtttt taagc                                35
```

<210> SEQ ID NO 126
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 126

```
ttgaccgtag tatacccccg gtcgtgtagc ggtga                                35
```

<210> SEQ ID NO 127
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 127

```
gacgatgggc atgaaactgt ggtttgctcc acaga                                35
```

<210> SEQ ID NO 128
<211> LENGTH: 35
<212> TYPE: DNA
<213> ORGANISM: Artificial Sequence

```
<220> FEATURE:
<223> OTHER INFORMATION: DNA probe sequence for depletion of target RNA

<400> SEQUENCE: 128
aaatacgggc cctatttcaa agatttttag gggaa                                    35

<210> SEQ ID NO 129
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 129
gattatgagg gcgtgatcat gaaaggtgat aagct                                    35

<210> SEQ ID NO 130
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 130
tgttaggaaa agggcataca ggactaggaa gcaga                                    35

<210> SEQ ID NO 131
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 131
ttcctgagcg tctgagatgt tagtattagt tagtt                                    35

<210> SEQ ID NO 132
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 132
gaggactagg atgatggcgg gcaggatagt tcaga                                    35

<210> SEQ ID NO 133
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 133
gacctcgtct gttatgtaaa ggatgcgtag ggatg                                    35

<210> SEQ ID NO 134
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 134
gtaccattgg tggccaattg atttgatggt aaggg                                    35
```

<210> SEQ ID NO 135
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 135
ggagttgaag attagtccgc cgtagtcggt gtact                              35

<210> SEQ ID NO 136
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 136
gagtcgcagg tcgcctggtt ctaggaataa tgggg                              35

<210> SEQ ID NO 137
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 137
tgggctgggt tttactatat gataggcatg tgatt                              35

<210> SEQ ID NO 138
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 138
actatggtga gctcaggtga ttgatactcc tgatg                              35

<210> SEQ ID NO 139
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 139
aataagcagt gcttgaatta tttggtttcg gttgt                              35

<210> SEQ ID NO 140
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 140
ctctgaggct tgtaggaggg taaaatagag accca                              35

<210> SEQ ID NO 141
<211> LENGTH: 35
<212> TYPE: DNA
<213> ORGANISM: Artificial Sequence
<220> FEATURE:
<223> OTHER INFORMATION: DNA probe sequence for depletion of target RNA

```
<400> SEQUENCE: 141
tgagccgtag atgccgtcgg aaatggtgaa gggag                         35

<210> SEQ ID NO 142
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 142
aataatgacg tgaagtccgt ggaagcctgt ggcta                         35

<210> SEQ ID NO 143
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 143
aaatattagt tggcggatga agcagatagt gagga                         35

<210> SEQ ID NO 144
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 144
tcaggcggcg gcttcgaagc caaagtgatg tttgg                         35

<210> SEQ ID NO 145
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 145
ggagacatac agaaatagtc aaaccacatc tacaa                         35

<210> SEQ ID NO 146
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 146
gccggaggtc attaggaggg ctgagagggc ccctg                         35

<210> SEQ ID NO 147
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 147
tagtatgagg agcgttatgg agtggaagtg aaatc                         35

<210> SEQ ID NO 148
```

```
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 148
atcgcgccat cattggtata tggttagtgt gttgg                         35

<210> SEQ ID NO 149
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 149
gacaggtggt gtgtggtggc cttggtatgt gcttt                         35

<210> SEQ ID NO 150
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 150
ttctgaggta ataaatagga ttatcccgta tcgaa                         35

<210> SEQ ID NO 151
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 151
gctggagtgg taaaaggctc agaaaaatcc tgcga                         35

<210> SEQ ID NO 152
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 152
gcctgttggg ggccagtgcc ctcctaattg ggggg                         35

<210> SEQ ID NO 153
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 153
ggatgtgttt aggagtggga cttctagggg attta                         35

<210> SEQ ID NO 154
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 154
```
ctcagtgtgt agcctaggat acaggccttc agcac          35

<210> SEQ ID NO 155
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 155
cggggacttt cccctaggcg gaaaggggag gaaca          35

<210> SEQ ID NO 156
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 156
gtctacgtgc gtatgcacgt ggcactctct gcccg          35

<210> SEQ ID NO 157
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 157
atacgcttct tggcggactt tggagtggga agcgg          35

<210> SEQ ID NO 158
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 158
agctgacgga tgacgccccc gcgccacgcc gctca          35

<210> SEQ ID NO 159
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 159
ggttggtgcg cggacacgca ctgcctgcgt aacta          35

<210> SEQ ID NO 160
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 160
atcctccagc ctcagcctcc cgagtagctg ggact          35

<210> SEQ ID NO 161
<211> LENGTH: 35
<212> TYPE: DNA

```
<213> ORGANISM: Artificial Sequence
<220> FEATURE:
<223> OTHER INFORMATION: DNA probe sequence for depletion of target RNA

<400> SEQUENCE: 161
atcctcccac ctcagcctcc cgagtagctg ggact                              35

<210> SEQ ID NO 162
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 162
ggcatagcgc actacagccc agaactcctg gactc                              35

<210> SEQ ID NO 163
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 163
gtcaccatat tgatgccgaa cttagtgcgg acacc                              35

<210> SEQ ID NO 164
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 164
cccctcctta ggcaacctgg tggtccccg ctccc                               35

<210> SEQ ID NO 165
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 165
ggagttttga cctgctccgt ttccgacctg ggccg                              35

<210> SEQ ID NO 166
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 166
ggagttttga cctgctctgt ttccgacctg ggccg                              35

<210> SEQ ID NO 167
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 167
gtggctattc acaggcgcga tcccactact gatca                              35
```

<210> SEQ ID NO 168
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 168
agagacgggg tctcgctatg ttgcccaggc tggag                35

<210> SEQ ID NO 169
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 169
atggggtgac agatgtcgca gccagatcgc cctca                35

<210> SEQ ID NO 170
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 170
gcctagccag ccagatcagc cgaatcaacc ctggc                35

<210> SEQ ID NO 171
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 171
ggggatggtc gtcctcttcg accgagcgcg cagct                35

<210> SEQ ID NO 172
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 172
tactcgtata cccttgaccg aagaccggtc ctcct                35

<210> SEQ ID NO 173
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 173
cttgagagct tgtttggagg ttctagcagg ggagc                35

<210> SEQ ID NO 174
<211> LENGTH: 35
<212> TYPE: DNA
<213> ORGANISM: Artificial Sequence
<220> FEATURE:

<223> OTHER INFORMATION: DNA probe sequence for depletion of target RNA

<400> SEQUENCE: 174
cttggaagct tgactaccct acgttctcct acaaa					35

<210> SEQ ID NO 175
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 175
gactgccaca tgcagcgcct catttggatg tgtct					35

<210> SEQ ID NO 176
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 176
gatactacac ttgatcttag ccaaaaggcc gagaa					35

<210> SEQ ID NO 177
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 177
gtcctcggat agaggacgta tcagatatta aactg					35

<210> SEQ ID NO 178
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 178
cggagcaagc tcctattcca tctcctattt ccaaa					35

<210> SEQ ID NO 179
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 179
gtgcaccgtt cctggaagta ctgcaatacc aggtc					35

<210> SEQ ID NO 180
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 180
gcactcagct cgtggcccca ctgatgagct tccct					35

```
<210> SEQ ID NO 181
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 181
tcagaccttc ccaagggaca tgggagtgga gtgac                                35

<210> SEQ ID NO 182
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 182
ctcagggaga gccctgttag ggccgcctct ggccc                                35

<210> SEQ ID NO 183
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 183
cgcgcggagc cccgttctct gggaactcac ctccc                                35

<210> SEQ ID NO 184
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 184
gaagggcggg gtccacggca tctcctgccc agtct                                35

<210> SEQ ID NO 185
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 185
ctggccgtga gtctgttcca agctccggca aagga                                35

<210> SEQ ID NO 186
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 186
tgcggggtac ctcacctcag ccattgaact cactt                                35

<210> SEQ ID NO 187
<211> LENGTH: 35
<212> TYPE: DNA
<213> ORGANISM: Artificial Sequence
<220> FEATURE:
<223> OTHER INFORMATION: DNA probe sequence for depletion of target RNA
```

<400> SEQUENCE: 187
gcggaggaga gtagtctgaa ttgggttatg aggtc        35

<210> SEQ ID NO 188
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 188
cgcctgacct ccccgaggtt tcgtcttcaa tgcaa        35

<210> SEQ ID NO 189
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 189
ctgatggcca tctgctcccg ttcgtccact acacg        35

<210> SEQ ID NO 190
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 190
tcattgccca tatccagggc catgtgacgg aggtt        35

<210> SEQ ID NO 191
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 191
gttttgttgg aatcagcctt ctccatgatc ctgtc        35

<210> SEQ ID NO 192
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 192
gggcacactt aaccacttcc cagcatcttt gttgc        35

<210> SEQ ID NO 193
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 193
gacaacattc acaatggggg tggactgatg tgtgt        35

<210> SEQ ID NO 194
<211> LENGTH: 35

<212> TYPE: DNA
<213> ORGANISM: Artificial Sequence
<220> FEATURE:
<223> OTHER INFORMATION: DNA probe sequence for depletion of target RNA

<400> SEQUENCE: 194
aagagaccaa gagagaacaa aagacacaaa gtatt                                35

<210> SEQ ID NO 195
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 195
actcaagacc tcaaggagtt agagccacca aatga                                35

<210> SEQ ID NO 196
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 196
cgggcctctg caggttgcaa ctgtggtgga gccgc                                35

<210> SEQ ID NO 197
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 197
gtggaatgtc acagttttac aagaacaata ctgtg                                35

<210> SEQ ID NO 198
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 198
aagacggcac attttgagag attcagagcc tgaca                                35

<210> SEQ ID NO 199
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 199
tgtaattcca cattgtctaa tcatgaaatc ataaa                                35

<210> SEQ ID NO 200
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 200
tgttgtctca tcagtatgct actgtcatgg aaagt                                    35

<210> SEQ ID NO 201
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 201
caatactgag catgctttgt tgttgttctg ttgtt                                    35

<210> SEQ ID NO 202
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 202
gacaggaaaa aagtgacact actgcactttt tgctg                                   35

<210> SEQ ID NO 203
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 203
aatttcagcc aaacatatat tttgctggaa atgat                                    35

<210> SEQ ID NO 204
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 204
ctctccaaaa catagccatc aaaagcagca aacaa                                    35

<210> SEQ ID NO 205
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 205
tggttagtaa gagtcagcct tataaaattt acatc                                    35

<210> SEQ ID NO 206
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 206
aggaggaatt taatattaca tgctataatg atatt                                    35

<210> SEQ ID NO 207
<211> LENGTH: 35
<212> TYPE: DNA
<213> ORGANISM: Artificial Sequence

```
<220> FEATURE:
<223> OTHER INFORMATION: DNA probe sequence for depletion of target RNA

<400> SEQUENCE: 207
ttttaataat tttaaactag ctacaaaatg tcaat                              35

<210> SEQ ID NO 208
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 208
tcattgcgca tgtctgcgtc ttcggccatg gtagc                              35

<210> SEQ ID NO 209
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 209
cgggtgcttt ccagcgactc atcagccaac tggtc                              35

<210> SEQ ID NO 210
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 210
aacataacca aagtcctgat accagcatct ttact                              35

<210> SEQ ID NO 211
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 211
cacacacaaa gcccgcagaa ttttcctagg tccgt                              35

<210> SEQ ID NO 212
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 212
tcctgattat tgccccaggc tttttgtaa gcatc                               35

<210> SEQ ID NO 213
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 213
agtaacacac tatagaaatg atccctgaaa gtata                              35
```

<210> SEQ ID NO 214
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 214
cagcatcccc cgcctcgcgc caagactaaa attaa                                35

<210> SEQ ID NO 215
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 215
atgggagaaa acgcaaaaag agacaatagg aggtg                                35

<210> SEQ ID NO 216
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 216
gagtggcggg cgggaaacgg cgacaaaaga gggag                                35

<210> SEQ ID NO 217
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 217
cagacagaac aagagacccg gagaccccgt ctggg                                35

<210> SEQ ID NO 218
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 218
aggagccgag atcgcgccac tgcaatccag ccggg                                35

<210> SEQ ID NO 219
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 219
aggcgggaga ctcgcttgag cccgggaggc agatg                                35

<210> SEQ ID NO 220
<211> LENGTH: 35
<212> TYPE: DNA
<213> ORGANISM: Artificial Sequence
<220> FEATURE:
<223> OTHER INFORMATION: DNA probe sequence for depletion of target RNA

```
<400> SEQUENCE: 220
ggcgtgtgcg cctttaagcc ccggctactc gggag                                35

<210> SEQ ID NO 221
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 221
cgtggttttc ggtgctctac acgttcagag aaact                                35

<210> SEQ ID NO 222
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 222
gccggcttca cgctcaggag aaaacgctac ctctc                                35

<210> SEQ ID NO 223
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 223
tcaatggctg acggcagttg cagccaagca acgcc                                35

<210> SEQ ID NO 224
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 224
ctctccctct cactccccaa tacggagaga agaac                                35

<210> SEQ ID NO 225
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 225
cattgagcca tcaagaagga aaaaccactc agacc                                35

<210> SEQ ID NO 226
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 226
cagcccagaa acgccccgga gtttacgagc tagtc                                35

<210> SEQ ID NO 227
```

```
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 227
aggcgaaaac ctttctcgcg acatgccaag cagga                              35

<210> SEQ ID NO 228
<211> LENGTH: 35
<212> TYPE: DNA
<213> ORGANISM: Artificial Sequence
<220> FEATURE:
<223> OTHER INFORMATION: DNA probe sequence for depletion of target RNA

<400> SEQUENCE: 228
caccccgaga aacccaaga gccgtcaccg ctgaa                               35

<210> SEQ ID NO 229
<211> LENGTH: 299
<212> TYPE: DNA
<213> ORGANISM: Homo sapiens

<400> SEQUENCE: 229
gccgggcgcg gtggcgcgtg cctgtagtcc cagctactcg ggaggctgag gctggaggat    60
cgcttgagtc caggagttct gggctgtagt gcgctatgcc gatcgggtgt ccgcactaag   120
ttcggcatca atatggtgac ctcccgggag cggggacca ccaggttgcc taaggagggg   180
tgaaccggcc caggtcggaa acggagcagg tcaaaactcc cgtgctgatc agtagtggga   240
tcgcgcctgt gaatagccac tgcactccag cctgggcaac atagcgagac cccgtctct    299

<210> SEQ ID NO 230
<211> LENGTH: 332
<212> TYPE: DNA
<213> ORGANISM: Homo sapiens

<400> SEQUENCE: 230
ggatgtgagg gcgatctggc tgcgacatct gtcaccccat tgatcgccag ggttgattcg    60
gctgatctgg ctggctaggc gggtgtcccc ttcctccctc accgctccat gtgcgtccct   120
cccgaagctg cgcgctcggt cgaagaggac gaccatcccc gatagaggag gaccggtctt   180
cggtcaaggg tatacgagta gctgcgctcc cctgctagaa cctccaaaca agctctcaag   240
gtccatttgt aggagaacgt agggtagtca agcttccaag actccagaca catccaaatg   300
aggcgctgca tgtggcagtc tgcctttctt tt                                 332

<210> SEQ ID NO 231
<211> LENGTH: 295
<212> TYPE: DNA
<213> ORGANISM: Homo sapiens

<400> SEQUENCE: 231
gccgggcaca gtggcgcgtg cctgtagtcc cagctactcg ggaggctgag gtgggaggat    60
cgcttgagcc caggagttct gggctgtagt gcgctatgcc gatcgggtgt ccgcactaag   120
ttcggcatca atatggtgac ctcccgggag cggggacca ccaggttgcc taaggagggg   180
tgaaccggcc caggtcggaa acagagcagg tcaaaactcc cgtgctgatc aggagacaga   240
gtttgtgagc agacaactgg tctgaccaaa atttatgagg tgggaatttc ctctt       295
```

<210> SEQ ID NO 232
<211> LENGTH: 321
<212> TYPE: DNA
<213> ORGANISM: Homo sapiens

<400> SEQUENCE: 232

```
gccgggcgcg gtggcgcgtg cctgtggtcc cagctactcg ggaggctgag gctggaggat    60
cgcttgagtc caggagttct gggctgtagt gcgctatgcc gatcgggtgt ccgcactaag   120
ttcggcatca atatggtgac ctcccgggag cgggggacca ccaggttgcc taaggagggg   180
tgaaccggcc caggtcggaa acggagcagg tcaaaactcc cgtgctgatc agtagaagtc   240
tgtaatgcta ctggtgtccc ctaattttct tatagccaca gttcctttcg cctgagctca   300
ttacagagac aaatatccat t                                             321
```

<210> SEQ ID NO 233
<211> LENGTH: 333
<212> TYPE: DNA
<213> ORGANISM: Homo sapiens

<400> SEQUENCE: 233

```
ggcggaggga agctcatcag tggggccacg agctgagtgc gtcctgtcac tccactccca    60
tgtcccttgg gaaggtctga gactagggcc agaggcggcc ctaacagggc tctccctgag   120
cttcggggag gtgagttccc agagaacggg gctccgcgcg aggtcagact gggcaggaga   180
tgccgtggac cccgccnttc ggggaggggc ccggcggatg cctcctttgc cggagcttgg   240
aacagactca cggccagcga agtgagttca atggctgagg tgaggtaccc cgcaggggac   300
ctcataaccc aattcagact actctcctcc gcc                                333
```

<210> SEQ ID NO 234
<211> LENGTH: 277
<212> TYPE: DNA
<213> ORGANISM: Homo sapiens

<400> SEQUENCE: 234

```
ggttcgtgct gaaggcctgt atcctaggct acacactgag gactctgttc ctcccctttc    60
cgcctagggg aaagtcccg gacctcgggc agagagtgcc acgtgcatac gcacgtagac   120
attccccgct tcccactcca aagtccgcca agaagcgtat cccgctgagc ggcgtggcgc   180
gggggcgtca tccgtcagct ccctctagtt acgcaggcag tgcgtgtccg cgcaccaacc   240
acacggggct cattctcagc gcggctgtaa aaaaaaa                            277
```

<210> SEQ ID NO 235
<211> LENGTH: 191
<212> TYPE: DNA
<213> ORGANISM: Homo sapiens

<400> SEQUENCE: 235

```
atcgcttctc ggccttttgg ctaagatcaa gtgtagtatc tgttcttatc agtttaatat    60
ctgatacgtc ctctatccga ggacaatata ttaaatggat ttttggaaat aggagatgga   120
ataggagctt gctccgtcca ctccacgcat cgacctggta ttgcagtact tccaggaacg   180
gtgcactctc c                                                        191
```

<210> SEQ ID NO 236
<211> LENGTH: 699
<212> TYPE: DNA
<213> ORGANISM: Homo sapiens

```
<400> SEQUENCE: 236
aagactatac tttcagggat catttctata gtgtgttact agagaagttt ctctgaacgt      60
gtagagcacc gaaaaccacg aggaagagag gtagcgtttt ctcctgagcg tgaagccggc     120
tttctggcgt tgcttggctg caactgccgt cagccattga tgatcgttct tctctccgta     180
ttggggagtg agagggagag aacgcggtct gagtggtttt tccttcttga tggctcaatg     240
acagagacta gctcgtaaac tccggggcgt ttctgggctg ttcgctcctg cttggcatgt     300
cgcgagaaag gttttcgcct cctgtttcag cggtgacggc tcttgggttt tctcggggtg     360
gcttttaat tttagtcttg gcgcgaggcg ggggatgctg tgtggcacct cctattgtct     420
cttttttgcgt tttctcccat tctcgctccc tcttttgtcg ccgtttcccg cccgccactc     480
ccaccccag acgggtctc cgggtctctt gttctgtctg ccggcccgg ctggattgca     540
gtggcgcgat ctcggctcct agcaacatct gcctcccggg ctcaagcgag tctcccgcct     600
aagccctccc gagtagccgg ggcttaaagg cgcacacgcc actccaggct ttttttttt     660
tttttttttt ttttttggca gaaacggggt gtcagcatg                            699

<210> SEQ ID NO 237
<211> LENGTH: 1542
<212> TYPE: DNA
<213> ORGANISM: Homo sapiens

<400> SEQUENCE: 237
atgttcgccg accgttgact attctctaca aaccacaaag acattggaac actataccta      60
ttattcggcg catgagctgg agtcctaggc acagctctaa gcctccttat tcgagccgag     120
ctgggccagc caggcaacct tctaggtaac gaccacatct acaacgttat cgtcacagcc     180
catgcatttg taataatctt cttcatagta atacccatca taatcggagg ctttggcaac     240
tgactagttc ccctaataat cggtgccccc gatatggcgt tccccgcat aaacaacata     300
agcttctgac tcttacctcc ctctctccta ctcctgctcg catctgctat agtggaggcc     360
ggagcaggaa caggttgaac agtctaccct cccttagcag ggaactactc ccaccctgga     420
gcctccgtag acctaaccat cttctcctta cacctagcag gtgtctcctc tatcttaggg     480
gccatcaatt tcatcacaac aattatcaat ataaaacccc ctgccataac ccaataccaa     540
acgcccctct tcgtctgatc cgtcctaatc acagcagtcc tacttctcct atctctccca     600
gtcctagctg ctggcatcac tatactacta acagaccgca acctcaacac caccttcttc     660
gaccccgccg gaggaggaga ccccattcta taccaacacc tattctgatt tttcggtcac     720
cctgaagttt atattcttat cctaccaggc ttcggaataa tctcccatat tgtaacttac     780
tactccggaa aaaagaacc atttggatac ataggtatgg tctgagctat gatatcaatt     840
ggcttcctag ggtttatcgt gtgagcacac catatattta cagtaggaat agacgtagac     900
acacgagcat atttcacctc cgctaccata atcatcgcta tccccaccgg cgtcaaagta     960
tttagctgac tcgccacact ccacggaagc aatatgaaat gatctgctgc agtgctctga    1020
gccctaggat tcatctttct tttcaccgta ggtggcctga ctggcattgt attagcaaac    1080
tcatcactag acatcgtact acacgacacg tactacgttg tagcccactt ccactatgtc    1140
ctatcaatag gagctgtatt tgccatcata ggaggcttca ttcactgatt tccctattc    1200
tcaggctaca ccctagacca aacctacgcc aaaatccatt tcactatcat attcatcggc    1260
gtaaatctaa ctttcttccc acaacacttt ctcggcctat ccggaatgcc ccgacgttac    1320
tcggactacc ccgatgcata caccacatga aacatcctat catctgtagg ctcattcatt    1380
```

```
tctctaacag cagtaatatt aataattttc atgatttgag aagccttcgc ttcgaagcga    1440
aaagtcctaa tagtagaaga accctccata aacctggagt gactatatgg atgccccca     1500 ccctaccaca cattcgaaga acccgtatac ataaaatcta ga                       1542
```

<210> SEQ ID NO 238
<211> LENGTH: 784
<212> TYPE: DNA
<213> ORGANISM: Homo sapiens

<400> SEQUENCE: 238

```
atgacccacc aatcacatgc ctatcatata gtaaaaccca gcccatgacc cctaacaggg    60
gccctctcag ccctcctaat gacctccggc ctagccatgt gatttcactt ccactccata    120
acgctcctca tactaggcct actaaccaac acactaacca tataccaatg atggcgcgat    180
gtaacacgag aaagcacata ccaaggccac cacacaccac ctgtccaaaa aggccttcga    240
tacgggataa tcctatttat tacctcagaa gttttttttct tcgcaggatt tttctgagcc    300
ttttaccact ccagcctagc cctacccccc aattaggag ggcactggcc cccaacaggc    360
atcaccccgc taaatcccct agaagtccca ctcctaaaca catccgtatt actcgcatca    420
ggagtatcaa tcacctgagc tcaccatagt ctaatagaaa acaaccgaaa ccaaataatt    480
caagcactgc ttattacaat tttactgggt ctctatttta ccctcctaca agcctcagag    540
tacttcgagt ctccctttcac catttccgac ggcatctacg gctcaacatt ttttgtagcc    600
acaggcttcc acggacttca cgtcattatt ggctcaactt tcctcactat ctgcttcatc    660
cgccaactaa tatttcactt tacatccaaa catcactttg gcttcgaagc cgccgcctga    720
tactggcatt ttgtagatgt ggtttgacta tttctgtatg tctccatcta ttgatgaggg    780
tctt                                                                 784
```

<210> SEQ ID NO 239
<211> LENGTH: 684
<212> TYPE: DNA
<213> ORGANISM: Homo sapiens

<400> SEQUENCE: 239

```
atggcacatg cagcgcaagt aggtctacaa gacgctactt cccctatcat agaagagctt    60
atcacctttc atgatcacgc cctcataatc attttcctta tctgcttcct agtcctgtat    120
gcccttttcc taacactcac aacaaaacta actaatacta acatctcaga cgctcaggaa    180
atagaaaccg tctgaactat cctgcccgcc atcatcctag tcctcatcgc cctcccatcc    240
ctacgcatcc tttacataac agacgaggtc aacgatccct cccttaccat caaatcaatt    300
ggccaccaat ggtactgaac ctacgagtac accgactacg gcggactaat cttcaactcc    360
tacatacttc ccccattatt cctagaacca ggcgacctgc gactccttga cgttgacaat    420
cgagtagtac tcccgattga agcccccatt cgtataataa ttacatcaca agacgtcttg    480
cactcatgag ctgtccccac attaggctta aaaacagatg caattcccgg acgtctaaac    540
caaaccactt tcaccgctac acgaccgggg gtatactacg gtcaatgctc tgaaatctgt    600
ggagcaaacc acagtttcat gcccatcgtc ctagaattaa ttccctaaa aatctttgaa    660 atagggcccg tatttaccct atag                                           684
```

<210> SEQ ID NO 240
<211> LENGTH: 2300
<212> TYPE: DNA

<213> ORGANISM: Homo sapiens

<400> SEQUENCE: 240

```
ggacaacacc ttcaaagaca ggccctctga gtccgacgag ctccagacca tccaagaaga      60
cagtgcagcc acctccgaga gcctggatgt gatggcgtca cagaagagac cctcccagag     120
gcacggatcc aagtacctgg ccacagcaag taccatggac catgccaggc atggcttcct     180
cccaaggcac agagacacgg gcatccttga ctccatcggg cgcttctttg gcggtgacag     240
gggtgcgccc aagcggggct ctggcaaggt accctggcta agccgggcc ggagccctct      300
gccctctcat gcccgcagcc agcctgggct gtgcaacatg tacaaggact cacaccaccc     360
ggcaagaact gctcactacg gctccctgcc ccagaagtca cacggccgga cccaagatga     420
aaacccgta gtccacttct tcaagaacat tgtgacgcct cgcacaccac cccgtcgca      480
gggaaagggg agaggactgt ccctgagcag atttagctgg ggggccgaag ccagagacc      540
aggatttggc tacggaggca gagcgtccga ctataaatcg gctcacaagg gattcaaggg     600
agtcgatgcc cagggcacgc tttccaaaat ttttaagctg ggaggaagag atagtcgctc     660
tggatcaccc atggctagac gctgaaaacc cacctggttc cggaatcctg tcctcagctt     720
cttaatataa ctgccttaaa actttaatcc cacttgcccc tgttacctaa ttagagcaga     780
tgaccctcc cctaatgcct gcggagttgt gcacgtagta gggtcaggcc acggcagcct      840
accggcaatt tccggccaac agttaaatga aacatgaaa acagaaacg gttaaaactg       900
tcccttctg tgtgaagatc acgttccttc ccccgcaatg tgcccccaga cgcacgtggg      960
tcttcagggg gccaggtgca cagacgtccc tccacgttca cccctccacc cttggacttt    1020
cttttcgccg tggctgcggc acccttgcgc ttttgctggt cactgccatg gaggcacaca    1080
gctgcagaga cagagaggac gtgggcggca gagaggactg ttgacatcca gcttccttt     1140
gttttttttt cctgtccttc tctcacctcc taaagtagac ttcattttc ctaacaggat     1200
tagacagtca aggagtggct tactacatgt gggagctttt ggtatgtgac atgcgggctg    1260
ggcagctgtt agagtccaac gtggggcagc acagagaggg ggccacctcc ccaggccgtg    1320
gctgcccaca cccccaatt agctgaattc gcgtgtggca gagggaggaa aaggaggcaa     1380
acgtgggctg ggcaatggcc tcacatagga aacagggtct tcctggagat tggtgatgg     1440
agatgtcaag caggtggcct ctggacgtca ccgttgccct gcatggtggc cccagagcag    1500
cctctatgaa caacctcgtt tccaaaccac agcccacagc cggagagtcc aggaagactt    1560
gcgcactcag agcagaaggg taggagtcct ctagacagcc tcgcagccgc gccagtcgcc    1620
catagacact ggctgtgacc gggcgtgctg gcagcggcag tgcacagtgg ccagcactaa    1680
ccctccctga aagataacc ggctcattca cttcctccca gaagacgcgt ggtagcgagt     1740
aggcacaggc gtgcacctgc tcccgaatta ctcaccgaga cacgggct gagcagacgg      1800
ccccgtggat ggagacaaag agctcttctg accatatcct tcttaacacc cgctggcatc    1860
tccttttcgcg cctccctccc taacctactg acccaccttt tgatttagc gcacctgtga    1920
ttgataggcc ttccaaagag tcccacgctg gcatcaccct cccgaggac ggagatgagg     1980
agtagtcagc gtgatgccaa aacgcgtctt cttaatccaa ttctaattct gaatgtttcg    2040
tgtgggctta ataccatgtc tattaatata tagcctcgat gatgagagag ttacaaagaa    2100
caaaactcca gacacaaacc tccaaatttt tcagcagaag cactctgcgt cgctgagctg    2160
aggtcggctc tgcgatccat acgtggccgc acccacacag cacgtgctgt gacgatggct    2220
gaacggaaag tgtacactgt tcctgaatat tgaaataaaa caataaactt ttaatggtaa    2280
```
aaaaaaaaaa aaaaaaaaaa                                                2300

<210> SEQ ID NO 241
<211> LENGTH: 2069
<212> TYPE: DNA
<213> ORGANISM: Homo sapiens

<400> SEQUENCE: 241
catctttgat gagggcagag ctcacgttgc attgaagacg aaacctcggg gaggtcaggc   60
gctgtctttc cttccctccc tgctcggcgg ctccaccaca gttgcaacct gcagaggccc  120
ggagaacaca accctcccga gaagcccagg tccagagcca aacccgtcac tgaccccccc a  180
gcccaggcgc ccagccactc cccaccgcta ccatggccga agacgcagac atgcgcaatg  240
agctggagga gatgcagcga agggctgacc agttggctga tgagtcgctg gaaagcaccc  300
gtcgtatgct gcaactggtt gaagagagta agatgctgg tatcaggact ttggttatgt  360
tggatgaaca aggagaacaa ctggaacgca ttgaggaagg gatggaccaa atcaataagg  420
acatgaaaga agcagaaaag aatttgacgg acctaggaaa attctgcggg ctttgtgtgt  480
gtccctgtaa caagcttaaa tcaagtgatg cttacaaaaa agcctgggc aataatcagg  540
acggagtggt ggccagccag cctgctcgtg tagtggacga acgggagcag atggccatca  600
gtggcggctt catccgcagg gtaacaaatg atgcccgaga aaatgaaatg gatgaaaacc  660
tagagcaggt gagcggcatc atcgggaacc tccgtcacat ggccctggat atgggcaatg  720
agatcgatac acagaatcgc cagatcgaca ggatcatgga gaaggctgat tccaacaaaa  780
ccagaattga tgaggccaac aacgtgcaa caaagatgct gggaagtggt taagtgtgcc  840
cacccgtgtt ctcctccaaa tgctgtcggg caagatagcc ccttcatgct tttctcatgg  900
tattatctag taggtctgca cacataacac acatcagtcc accccattg tgaatgttgt  960
cctgtgtcat ctgtcagctt cccaacaata cttttgtgtct tttgttctct cttggtctct 1020
ttctttccaa aggttgtaca tagtggtcat ttggtggctc taactccttg aggtcttgag 1080
tttcattttt catttctctt cctcggtggc atttgctgaa taacaacaat ttaggaatgc 1140
tcaatgtgct gttgattctt tcaatccaca gtattgttct tgtaaaactg tgacattcca 1200
cagagttact gccacggtcc tttgagtgtc aggctctgaa tctctcaaaa tgtgccgtct 1260
ttggttcctc atggctgtta tctgtctta tgatttcatg attagacaat gtggaattac 1320
ataacaggca ttgcactaaa agtgatgtga tttatgcatt tatgcatgag aactaaatag 1380
attttttagat tcctacttaa acaaaaactt tccatgacag tagcatactg atgagacaac 1440
acacacacac acaaaacaac agcaacaaca acagaacaac aacaaagcat gctcagtatt 1500
gagacactgt caagattaag ttataccagc aaaagtgcag tagtgtcact ttttcctgt 1560
caatatatag agacttctaa atcataatca tccttttta aaaaaagaa ttttaaaaaa 1620
gatggatttg acacactcac catttaatca tttccagcaa aatatatgtt tggctgaaat 1680
tatgtcaaat ggatgtaata tagggtttgt ttgctgcttt tgatggctat gttttggaga 1740
gagcaatctt gctgtgaaac agtgtggatg taaattttat aaggctgact cttactaacc 1800
accatttccc ctgtggtttg ttatcagtac aattctttgt tgcttaatct agagctatgc 1860
acaccaaatt gctgagatgt ttagtagctg ataaagaaac cttttaaaaa aataatataa 1920
atgaatgaaa tataaactgt gagataaata tcattatagc atgtaatatt aaattcctcc 1980
tgtctcctct gtcagtttgt gaagtgattg acattttgta gctagtttaa aattattaaa 2040

| aattatagac tccaaaaaaa aaaaaaaaa | 2069 |

<210> SEQ ID NO 242
<211> LENGTH: 1513
<212> TYPE: DNA
<213> ORGANISM: Homo sapiens

<400> SEQUENCE: 242

| gcctcaagac cttgggctgg gactggctga gcctggcggg aggcggggtc cgagtcaccg | 60 |
| cctgccgccg cgccccggt ttctataaat tgagcccgca gcctcccgct tcgctctctg | 120 |
| ctcctcctgt tcgacagtca gccgcatctt cttttgcgtc gccaggtgaa gacgggcgga | 180 |
| gagaaacccg ggaggctagg gacggcctga aggcggcagg ggcgggcgca ggccggatgt | 240 |
| gttcgcgccg ctgcgggccg agccacatcg ctcagacacc atggggaagg tgaaggtcgg | 300 |
| agtcaacgga tttggtcgta ttgggcgcct ggtcaccagg gctgcttta actctggtaa | 360 |
| agtggatatt gttgccatca atgacccctt cattgacctc aactacatgg tttacatgtt | 420 |
| ccaatatgat tccacccatg gcaaattcca tggcaccgtc aaggctgaga cgggaagct | 480 |
| tgtcatcaat ggaaatccca tcaccatctt ccaggagcga gatcccctcca aaatcaagtg | 540 |
| gggcgatgct ggcgctgagt acgtcgtgga gtccactggc gtcttcacca ccatggagaa | 600 |
| ggctggggct catttgcagg ggggagccaa aagggtcatc atctctgccc cctctgctga | 660 |
| tgcccccatg ttcgtcatgg gtgtgaacca tgagaagtat gacaacagcc tcaagatcat | 720 |
| cagcaatgcc tcctgcacca ccaactgctt agcacccctg gccaaggtca tccatgacaa | 780 |
| ctttggtatc gtggaaggac tcatgaccac agtccatgcc atcactgcca cccagaagac | 840 |
| tgtggatggc ccctccggga actgtggcg tgatggccgc ggggctctcc agaacatcat | 900 |
| ccctgcctct actggcgctg ccaaggctgt gggcaaggtc atccctgagc tgaacgggaa | 960 |
| gctcactggc atggccttcc gtgtccccac tgccaacgtg tcagtggtgg acctgacctg | 1020 |
| ccgtctagaa aaacctgcca atatgatga catcaagaag gtggtgaagc aggcgtcgga | 1080 |
| gggccccctc aagggcatcc tgggctacac tgagcaccag gtggtctcct ctgacttcaa | 1140 |
| cagcgacacc cactcctcca cctttgacgc tgggctggc attgccctca cgaccactt | 1200 |
| tgtcaagctc atttcctggt atgacaacga atttggctac agcaacaggg tggtggacct | 1260 |
| catgccccac atggcctcca aggagtaaga cccctggacc accagcccca gcaagagcac | 1320 |
| aagaggaaga gagagaccct cactgctggg gagtccctgc cacactcagt cccccaccac | 1380 |
| actgaatctc ccctcctcac agttgccatg tagacccctt gaagagggga ggggcctagg | 1440 |
| gagccgcacc ttgtcatgta ccatcaataa agtaccctgt gctcaaccag ttaaaaaaa | 1500 |
| aaaaaaaaa aaa | 1513 |

<210> SEQ ID NO 243
<211> LENGTH: 299
<212> TYPE: DNA
<213> ORGANISM: Homo sapiens

<400> SEQUENCE: 243

| gccgggcgcg gtggcgcgtg cctgtagtcc cagctactcg ggaggctgag gtgggaggat | 60 |
| cgcttgagcc caggagttct gggctgtagt gcgctatgcc gatcgggtgt ccgcactaag | 120 |
| ttcggcatca atatggtgac ctcccgggag cggggaccac ccaggttgcc taaggagggg | 180 |

```
tgaaccggcc caggtcggaa acggagcagg tcaaaactcc cgtgctgatc agtagtggga    240
tcgcgcctgt gaatagccac tgcactccag cctgagcaac atagcgagac cccgtctct     299
```

SYSTEM AND METHOD FOR TARGETED DEPLETION OF NUCLEIC ACIDS

CROSS-REFERENCE TO RELATED APPLICATIONS

This application is a continuation application of, and incorporates herein by reference, U.S. patent application Ser. No. 15/423,850, filed Feb. 3, 2017, which is based on, claims the benefit of, and incorporates herein by reference, U.S. Provisional Patent Application No. 62/295,307 filed Feb. 15, 2016, and entitled, "System and Method for Targeted Depletion of Nucleic Acids".

STATEMENT REGARDING FEDERALLY SPONSORED RESEARCH

Not applicable.

BACKGROUND OF THE INVENTION

The disclosure relates, in general, to targeted depletion of nucleic acids and, more particularly, to a system and method for degrading selected nucleic acids polymers amongst a broader population of nucleic adds.

Whole transcriptome sequencing, also known as RNA-sequencing or RNA-seq, is a useful technique for characterizing the total gene expression of a biological sample. In this technique, RNA (either total or poly-A selected) is converted into cDNA using reverse transcriptase, followed by second-strand synthesis, addition of sequencing adapters, and high-throughput sequencing. One challenge associated with this approach is that only a very few genes (e.g. less than about ten) account for the vast majority of transcripts expressed in any particular tissue or cell type. As a result, the major portion of a given set of sequencing reads are derived from the most highly expressed genes, whereas a small portion of the sequencing reads are derived from the genes having the lowest expression levels. For example, ribosomal RNA (rRNA) can represent 90% or more of the material in a human total RNA sample. For experiments where the remaining 10% or less of the material in the sample may be relevant for a given experiment the presence of rRNA can consume costly sequencing reagents, obscure the presence of low expression level transcripts, decrease experimental throughput, the like, or combinations thereof. The aforementioned approach to RNA-seq is therefore inefficient for studying the expression patterns and transcript structures of lowly expressed genes that may have important biological functions. Accordingly, what is needed is a new experimental approach that mitigates the detrimental effects that highly abundant transcripts can have on the efficient analysis of RNA.

SUMMARY OF THE INVENTION

The present invention overcomes the aforementioned drawbacks by providing a system and method for targeted depletion of nucleic acids.

In accordance with one embodiment of the present disclosure, a kit for depleting target nucleic acids from a nucleic acid sample includes a plurality of deoxyribonucleic acid (DNA) probes, each of the DNA probes hybridizable to form a heteroduplex with at least one of a plurality of target ribonucleic acid (RNA) transcripts in a nucleic acid sample, where the number of unique target RNA transcripts hybridized by the plurality of DNA probes is at least 3. The kit further includes an enzyme having RNA-DNA hybrid ribonucleotidohydrolase activity, where the enzyme degrades at least the RNA portion of the heteroduplex.

In one aspect the number of unique DNA probes is at least 10.

In one aspect the number of unique DNA probes is at least 100.

In another aspect, the fraction of the total number of bases of each target RNA transcript hybridizable by the DNA probes is at least 0.5.

In another aspect, the fraction of the total number of bases hybridizable by the DNA probes is at least 0.75.

In another aspect, the fraction of the total number of bases hybridizable by the DNA probes is at least 0.9.

In another aspect, the number of unique target RNA transcripts hybridized by the plurality of DNA probes is at least 10.

In another aspect, the number of unique target RNA transcripts hybridized by the plurality of DNA probes is at least 100.

In another aspect, the DNA probes are hybridizable along the length of each of the target RNA transcripts at a regular spacing, where for each pair of adjacently hybridizable DNA probes, the 3' end of a first one of the pair of DNA probes is spaced apart from the 5' end of a second one of the pair of DNA probes by a nucleotide interval relative to the target RNA transcript.

In another aspect the nucleotide interval is less than about 50.

In another aspect the nucleotide interval is less than about 10.

In accordance with another embodiment of the present disclosure; a method for depleting target nucleic acids from a nucleic acid sample includes hybridizing a plurality of deoxyribonucleic acid (DNA) probes with a plurality of target ribonucleic acid (RNA) transcripts in a nucleic acid sample, each of the DNA probes forming a heteroduplex with at least one of the plurality of target RNA transcripts. The method further includes treating the heteroduplex with an enzyme having RNA-DNA hybrid ribonucleotidohydrolase activity, thereby degrading at least the RNA portion of the heteroduplex. The number of unique target RNA transcripts hybridized by the plurality of DNA probes is at least 3.

In one aspect, the number of unique DNA probes is at least 10.

In one aspect, the number of unique DNA probes is at least 100.

In another aspect, the fraction of the total number of bases of each target RNA transcript hybridizable by the DNA probes is at least 0.5.

In another aspect, the fraction of the total number of bases hybridizable by the DNA probes is at least 0.75.

In another aspect, the fraction of the total number of bases hybridizable by the DNA probes is at least 0.9.

In another aspect, the number of unique target RNA transcripts hybridized by the plurality of DNA probes is at least 10.

In another aspect, the number of unique target RNA transcripts hybridized by the plurality of DNA probes is at least 100.

In another aspect the DNA probes are hybridizable along the length of each of the target RNA transcripts with a regular spacing, where for each pair of adjacently hybridizable DNA probes, the 3' end of a first one of the pair of DNA probes is spaced apart from the 5' end of a second one of the pair of DNA probes by a nucleotide interval relative to the target RNA transcript.

In another aspect, the nucleotide interval is less than about 50.

In another aspect the interval of nucleotides is less than about 10.

In another aspect the method further includes depleting the quantity of the target RNA transcripts by at least about 50%.

In another aspect, the method further includes depleting the quantity of the target RNA transcripts by at least about 80%.

In accordance with another embodiment of the present disclosure, a method for depleting target nucleic acids from a nucleic acid sample includes selecting a plurality of target ribonucleic acid (RNA) transcripts to deplete from a nucleic acid sample, each of the target RNA transcripts derived from a corresponding deoxyribonucleic acid (DNA) having a known sequence. The method further includes synthesizing a plurality of DNA probes hybridizable to form a heteroduplex with at least one of the plurality of target RNA transcripts, hybridizing the plurality of DNA probes with the target RNA transcripts in the nucleic acid sample, each of the DNA probes forming a heteroduplex with at least one of the plurality of target RNA transcripts, and treating the heteroduplex with an enzyme having RNA-DNA hybrid ribonucleotidohydrolase activity, thereby degrading at least the RNA portion of the heteroduplex. The number of unique target RNA transcripts hybridized by the plurality of DNA probes is at least 3.

In one aspect, the method further includes designing the plurality of DNA probes to hybridize along the length of each of the target RNA transcripts with a regular spacing wherein for each pair of adjacently hybridizable DNA probes, the 3' end of a first one of the pair of DNA probes is spaced apart from the 5' end of a second one of the pair of DNA probes by a nucleotide interval relative to the target RNA transcript.

In another aspect the nucleotide interval is less than about 50.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
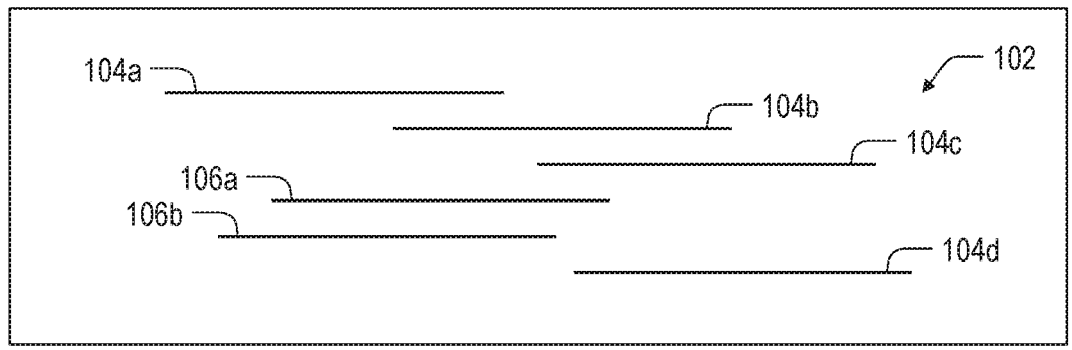
FIG. 1 is a schematic illustration showing a broad overview of a system and method for targeted depletion of nucleic acids according to the present disclosure.
Figure 1:
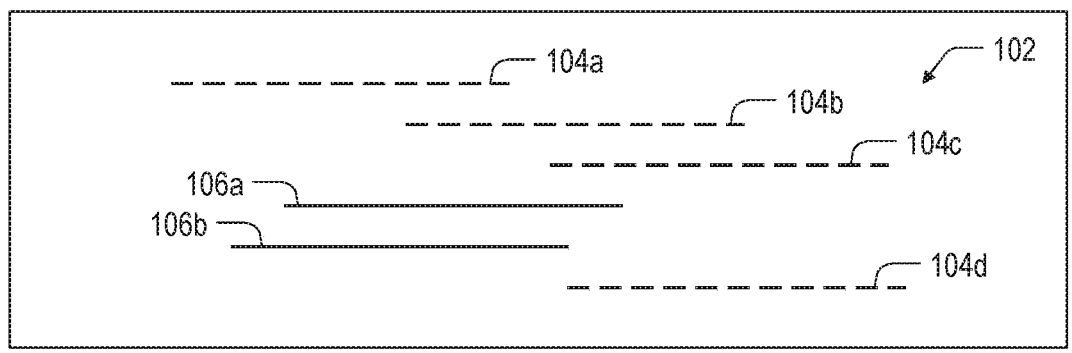
Figure 1:
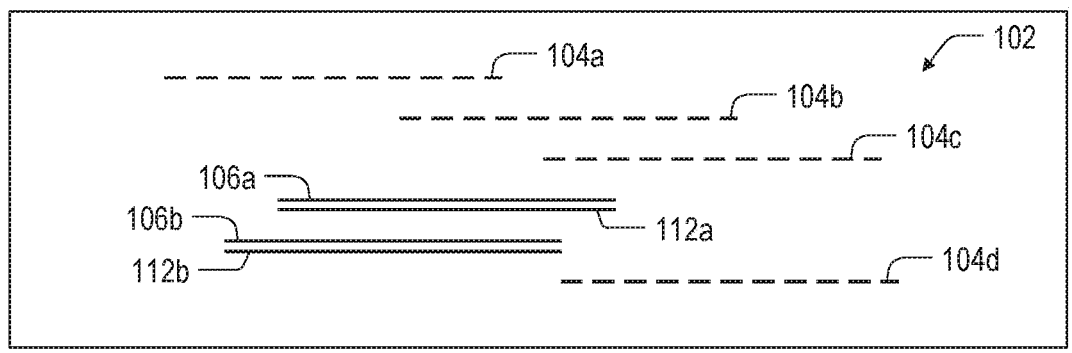

As also discussed above, in various situations it may be useful to employ techniques such as RNA-seq to determine the sequences and relative abundance of transcripts in an RNA sample. In general, RNA is first converted (e.g., reverse transcribed) into complementary DNA (cDNA), and then the cDNA is converted into double-stranded DNA (dsDNA), ligated to sequencing adapters, and sequenced. The sequencing reads, usually numbering in the millions, are analyzed using standard bioinformatics methods to determine which genes and transcript variants the sequencing reads represent. However, the relative abundance of different transcripts in an RNA sample can vary considerably between different cells and different tissues, at different developmental stages, and as a consequence of disease or environmental stimuli. This can present a significant challenge when the goal of an RNA-seq experiment is to study transcripts that are present in the sample at a much lower relative abundance, because most of the sequencing reads generated in an RNA-seq experiment are derived from high-abundance transcripts (e.g. rRNA molecules) while relatively few are derived from the transcripts of interest.

One approach to compensate for imbalances in transcript abundance is simply to generate more sequencing reads in the RNA-seq experiment so that an adequate amount of data for analysis can be obtained for lowly expressed transcripts of interest. However, increased sequencing imposes increased time and reagent requirements, thereby resulting in an inefficient and costly solution. Another approach to compensate for imbalances in transcript abundance is targeted depletion of individual high-abundance transcript such as rRNA or alpha-globin and beta-globin. Specific methods developed to exclusively deplete RNA samples prior to sequencing include: (1) hybridization of biotinylated capture probes to rRNA or alpha-globin and beta-globin, and removal of the hybridized complexes from the sample via binding to streptavidin-coated magnetic beads, (ii) poly-A RNA purification, which does not select for non-polyadenylated RNA molecules such as rRNA, and (iii) hybridization of DNA probes complementary to rRNA followed by enzymatic fragmentation of the RNA component of the DNA-RNA duplexes via RNase H treatment.

Each of the aforementioned rRNA depletion techniques are more or less effective for reducing sequencing reads derived from either rRNA or globin in RNA-seq experiments. Nonetheless, other categories of RNA molecules may still be much more highly expressed than the transcripts of interest. Accordingly, it may be useful to remove additional or alternative RNA molecules to further increase the proportion of sequencing reads derived from transcripts of interest. However, an efficient, targeted method for simultaneously depleting several (i.e., greater than two) of the most highly expressed transcripts from an RNA sample in an RNA-Seq workflow has not yet been demonstrated. Moreover, current commercial products for targeted depletion of rRNA or globin transcripts are specific for a particular source of RNA (e.g., human RNA), and consequently are not useful for treating RNA derived from other sources.

These and other challenges may be overcome with a system and method for targeted depletion of nucleic acids according to the present disclosure. In one embodiment of the present disclosure, a method is provided for depleting target nucleic acids from a nucleic acid sample. The method includes the use of a collection of DNA probes designed to selectively and specifically hybridize with multiple different target RNA transcripts in a nucleic acid sample. The resulting DNA:RNA heteroduplexes are then treated with an enzyme having RNA-DNA hybrid rIbonucleotidohydrolase activity to degrade the RNA portion of the heteroduplex, thereby depleting the target RNA transcripts from the nucleic acid sample while leaving the rest of the nucleic acid sample intact By enabling depletion of the target RNA transcripts, the untargeted RNA transcripts are enriched within the nucleic acid sample. The enriched nucleic acid sample permits more efficient downstream analysis as various reagents and other sequencing resources are not consumed or occupied by material derived from RNA transcripts of little to no experimental interest (e.g., highly expressed RNAs).

Embodiments of the present disclosure have several further advantages over known approaches for targeted depletion of RNA. In one aspect. DNA probes can be designed to target more than just one or two target RNA transcripts for depletion at a time. For example, embodiments of the present disclosure stem from the surprising discovery that DNA probes can be designed to target at least ten or more target RNA transcripts simultaneously. Further, the probes can be customized for a particular RNA sample derived from any cell or tissue as long as the nucleic acid sequences of the target RNA transcripts are known or can be determined. With respect to the DNA probes for targeted depletion, parameters such as the number, spacing, length, concentration, or combinations thereof can be tuned to achieve a specified degree of target RNA transcript depletion. For example, one or more of the aforementioned parameters can be varied according to the present disclosure in order to reduce the concentration of a target RNA transcript in a nucleic acid sample by up to 90% or greater.

Turning now to FIG. 1, a system and method for targeted nucleic acid depletion is broadly illustrated as including three phases. In a first phase 100, a nucleic acid sample 102 is provided for depletion of target RNA transcripts. The nucleic acid sample 102 includes a plurality of unique target RNA transcripts 104a, 104b, 104c, and 104d (collectively, target RNA transcripts 104), as well as a number of unique untargeted RNA transcripts 106a and 106b (collectively, untargeted RNA transcripts 106). While the nucleic acid sample 102 in FIG. 1, is illustrated as including only a few unique RNA transcripts, it will be appreciated that the nucleic acid sample 102 or another nucleic acid sample for use with the present disclosure can include any number of unique targeted or untargeted RNA transcripts. A unique RNA transcript is defined herein as an RNA transcript having a unique nucleic acid sequence or portion thereof. That is, a first RNA transcript derived, for example, from a first DNA sequence can be said to be unique relative to a second RNA transcript derived from a second DNA sequence different from the first DNA sequence. Notably, the two or more copies of an RNA transcript identically derived from the first DNA sequence would not be considered to be unique with respect to each other. Further, if the first RNA transcript was to become degraded, fragmented, or otherwise broken down into two or more constituent parts, then each of the individual parts of the first RNA transcript would not be considered to be unique RNA transcripts relative to one another.

With continued reference to FIG. 1, the present disclosure provides for targeted depletion of the target RNA transcripts 104, while leaving the untargeted RNA transcripts 106 intact. The result is that the untargeted RNA transcripts 106 are ultimately enriched within the nucleic acid sample 102. Accordingly, in a second phase 108, each of the target RNA transcripts 104 are selectively degraded (or otherwise depleted) as indicated by the dashed lines while the untargeted RNA transcripts 106 are left intact as indicated by the solid lines. To degrade the target RNA transcripts 104, a plurality of DNA probes (not shown) are specifically hybridized to the target RNA transcripts, and the resulting DNA:RNA heteroduplexes are treated with an enzyme (not shown) having RNA-DNA hybrid ribonucleotidohydrolase activity such that the enzyme degrades the RNA portion of the heteroduplex.

Finally, in a third phase 110, the nucleic acid sample 102 can be further prepared for sequencing or other downstream analysis. Treatment of the nucleic acid sample 102 will typically include first strand cDNA synthesis using the untargeted RNA transcripts 106 as templates. In particular, a first strand cDNA 112a can be prepared from the untargeted RNA transcript template 106a, while a first strand cDNA 112b can be prepared from the untargeted RNA transcript template 106b. In one aspect, the length (i.e., number of nucleotides) of each of the degraded target RNA transcripts 104 may be too small to be useful as templates for first strand cDNA synthesis. In another aspect, the untargeted RNA transcripts 106 may be purified away from the degraded target RNA transcripts (e.g. using a size-based separation technique) prior to first strand cDNA synthesis or other downstream treatment step.

Figure 2:
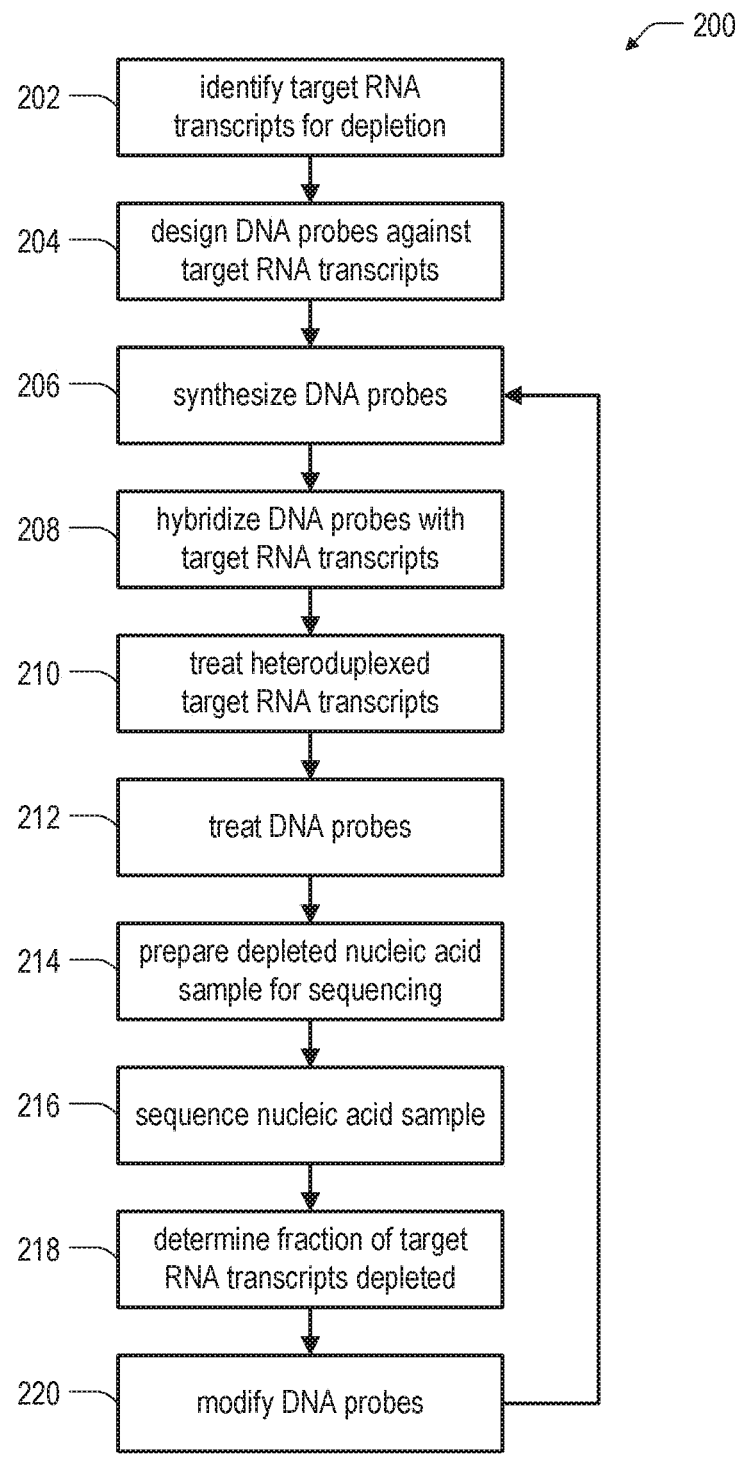
FIG. 2 is a schematic flow diagram illustrating an embodiment of a method for targeted depletion of target RNA transcripts from a nucleic acid sample.

Turning now to FIG. 2, a method 200 for targeted depletion of a nucleic acids is outlined in greater detail. A step 202 of the method 200 includes identifying target RNA transcripts for depletion from a larger nucleic acid sample. The nucleic acid sample can include RNA derived from any cell, tissue, or other source of RNA. The nucleic acid sample can further include additional components (e.g., DNA, protein, lipids, salts, or the like); however, it may be useful to purify the RNA away from one or more of the additional components in the case that these additional components interfere with or otherwise reduce the efficacy of the method 200. Examples of target RNA transcripts include highly expressed or abundant RNAs, ribosomal RNAs, pseudogene transcripts, untranslated RNAs, all known RNA transcripts, any RNA transcript that is not of interest for a particular experiment and combinations thereof. In general, any combination of RNA transcripts can be targeted for depletion within a nucleic acid sample, and the number and identity of the RNA transcripts targeted for depletion can vary depending on the nature of the experiment;

In order to identify the target RNA transcripts for depletion in the step 202, it may be useful to determine the predicted or actual coding sequences of the target RNA transcripts. As described with respect to FIG. 1, the target RNA transcripts are depleted through the use of an enzyme having RNA-DNA hybrid ribonucleotidohydrolase activity. To employ this approach, the target RNA transcripts are hybridized with complementary DNA probes while ensuring that the untargeted RNA transcripts remain as single stranded RNAs. That is, the untargeted RNA transcripts should generally not form heteroduplexes that are substrates for an enzyme having RNA-DNA hybrid ribonucleotidohydrolase activity. Therefore, in a step 204 of the method 200, it may be useful to determine the predicted or actual coding sequences of the target RNA transcripts to inform design of DNA probes against the target RNA transcripts. For a target RNA transcript where the nucleic acid sequence is known, DNA probes can be designed in any suitable manner in order to form a DNA:RNA heteroduplex with a target RNA, where the DNA:RNA heteroduplex is a substrate for an enzyme having RNA-DNA hybrid ribonucleotidohydrolase activity. For example, the DNA probes can have a variable or fixed length, can be designed to be complementary to all or a portion of the target RNA transcript, can include zero, one, or more mismatches, can include one or more chemical modifications, the like, or combinations thereof.

Following design of the DNA probes in the step 202, the method 200 can include a step 206 of synthesizing the designed DNA probes. The DNA probes can be synthesized using any known method. For example, the DNA probes can be prepared synthetically using solid phase synthesis methods such as column or array-based approaches including traditional mask-based photolithography or maskless array-based synthesis methods. One consideration for choosing a method for DNA probe synthesis relates to the fidelity of the synthesis method. Herein, DNA synthesis fidelity refers to the accuracy with which the probe designs are realized through DNA synthesis. A synthesized DNA probe that is identical to the sequence of the designed probe can be said to have been synthesized with 100% fidelity, whereas a ten nucleotide long DNA probe design that is synthesized with a total of three errors (i.e. insertions, deletions, substitutions, etc.) can be said to have been synthesized with 70% fidelity.

Factors such as the experimental conditions employed for hybridization, the characteristics of the enzyme having RNA-DNA hybrid ribonucleotidohydrolase activity, and experimental conditions employed for enzyme treatment can place limitations on the required fidelity of the DNA probes. In some embodiments, the nature of the selected enzyme and the experimental conditions employed can necessitate a high degree of fidelity (e.g., >95%), whereas other enzymes or conditions may afford the use of synthesis techniques with a lower degree of synthesis fidelity. For example, the minimum size of the DNA:RNA heteroduplex recognized by RNase HI from *Escherichia coli* has been reported to be a tetramer. Accordingly, when using the *E. coli* RNase HI enzyme, a selected DNA synthesis method should be capable of synthesizing on average at least four consecutive nucleotides with 100% fidelity. However, the overall fidelity of a thirty nucleotide DNA probe including the aforementioned four consecutive nucleotides may be less than 100% while still potentially resulting in an effective DNA probe for use according the present disclosure.

A step 208 of the method 200 includes hybridizing the DNA probes synthesized in the step 206 with a nucleic acid sample known (or at least suspected) to include the target RNA transcripts identified in the step 202. Achieving successful hybridization of the DNA probes with the target RNA transcripts in the step 208 depends on several parameters. Examples parameters include the complexity of the nucleic acid sample (e.g., number of unique RNA transcripts, transcript abundance, transcript nucleotide length distribution, transcript quality, and the like), DNA probe characteristics (e.g., total number of unique DNA probes, probe length, probe fidelity, number of probes per transcript, and the like), and characteristics of the hybridization reaction (e.g., temperature, time, choice of buffer, and the like). In one aspect, it may be useful to vary the concentration of the DNA probes based on an estimate of the quantity of the corresponding target RNA transcript. For example, it may be useful to provide a ratio of DNA probes to the corresponding target RNA transcript of between about $10^{-4}$:1 and about $10^3$:1 on a molar basis. That is, if a ratio of 10:1 DNA probe to target RNA transcript is chosen, then a hybridization mixture would include 10 copies (molecules) of each DNA probe for each copy (molecule) of the corresponding target RNA transcript Notably, conditions useful for implementation in the step 208 are generally in-line with typical DNA oligo/RNA transcript hybridization conditions known in the art.

With continued reference to FIG. 2, a step 210 of the method 200 includes treating the heteroduplexed target RNA transcripts with the ultimate goal of depleting the target RNA transcripts from the nucleic acid sample. One approach for treatment in the step 210 includes providing an enzyme having RNA-DNA hybrid ribonucleotidohydrolase activity in order to degrade at least the RNA portion of any target RNA transcripts that hybridized with DNA probes in the step 208. In one aspect degradation can involve breaking or modification of one or more chemical bonds that make up the target RNA transcripts. In the case of *E. coli* RNase HI and other RNase H-like enzymes, in general, the RNA strand of a DNA-RNA hybrid is cleaved yielding a 3'-hydroxyl and a 5'-phosphate at the hydrolysis site. The extent to which each target RNA transcript is cleaved by an RNase is at least in part dependent on factors discussed with respect to the step 204 and the step 208. However, parameters such as the identity of the RNase H or other like enzyme, and the treatment conditions (e.g., time, temperature, and the like) can also have an effect on depletion of the target RNA transcripts. Further, while an enzyme having RNA-DNA hybrid ribonucleotidohydrolase activity can be used in the step 210 to treat the heteroduplexed target RNA transcripts, other treatment methods can also be used. For example, an enzyme or other non-enzymatic chemistry enabling simultaneous cleavage of both RNA and DNA strands in the heteroduplex would also function to deplete the target RNA transcripts in the step 210. Notably, an RNase or other like enzyme or chemical conversion scheme should not have a deleterious effect on untargeted RNA transcripts. For example, an RNase should generally be provided that does not degrade or otherwise deplete RNA transcripts that are not hybridized with one or more DNA probes (i.e., untargeted RNA transcripts).

In a step 212 of the method 200, it may be useful to treat the DNA probes. For example, in the case that only the target RNA transcripts are degraded or otherwise depleted in the step 210, it may be useful to further treat the DNA probes. In one aspect, treatment of the DNA probes can include digestion of the DNA probes with an enzyme possessing DNase activity. In another aspect; treatment of the DNA probes can include selective capture, isolation, or purification of the DNA probes away from the remaining RNA transcripts in the nucleic acid sample. Moreover, it will be appreciated that the step 212 and additionally (or alternatively) other steps of the method 200 can include one or more clean-up or other like purification steps in order to accommodate the use of various enzymes, buffers, or other treatment conditions throughout the method 200. Example purification steps for recovery and clean-up of a nucleic acid sample that can be employed include the use of solid phase reversible immobilization (SPRI) beads, ethanol precipitation, silica membrane-based column purification, phenol-chloroform extraction, or any other suitable method.

The method 200 can further include a step 214 of preparing a nucleic acid sample depleted of target RNA transcripts for sequencing. A variety of method exist for preparing RNA libraries for sequencing, and the method selected will vary depending on how the sample will be sequenced. One approach suitable for implementation in the step 214 includes performing first strand cDNA synthesis using an enzyme having reverse transcriptase activity with the remaining (untargeted) RNA transcripts in the nucleic acid sample as a template. Thereafter, steps such as second strand synthesis, A-tailing, adapter ligation, and library amplification can be performed as required by the selected sequencing approach. Notably, the choice of sequencing method will dictate yet other additional or alternative steps that can be included in the step 214.

In a step 216 of the method 200, the depleted nucleic acid sample can be sequenced using any sequencing method. The step 216 can provide not only the sequence of each of the untargeted RNA transcripts in the nucleic acid sample, but also statistical data such as the relative abundance of each of the untargeted RNA transcripts. The step 216 can also provide information related to the efficacy of the method 200 for depleting the target RNA transcripts in the nucleic acid sample. Accordingly, a step 218 of the method can include determining what fraction or percent of the target RNA transcripts were depleted from the nucleic acid. In some example cases, the method 200 can effectively deplete a given target RNA transcript such that no copies of the transcript are detected through analysis of the sequencing data produced in the step 216. However, in other case, the method 200 can result in insufficient depletion of a target RNA transcript as determined by the particular goals of an experimental method. In one aspect, insufficient depletion can include a determination that a reduction of target RNA transcript of less than an order of magnitude was achieved. In such a case, a step 220 of the method can include modification of one or more aspects of the DNA probes used for targeted depletion. Modification such as the number of DNA probes per transcript, the length, or spacing of the DNA probes, or modifications to other of the aforementioned parameters can be made. The method 200 can then return to the step 206 (or alternatively another one of the steps 202-218 in the method 200) to implement the modifications to the DNA probes. Importantly, modifications to reaction conditions, choice of treatments for RNA or DNA depletion, or the like can be made in order to the tailor the method 200 to achieve a desired degree of target RNA depletion.

Figure 3:
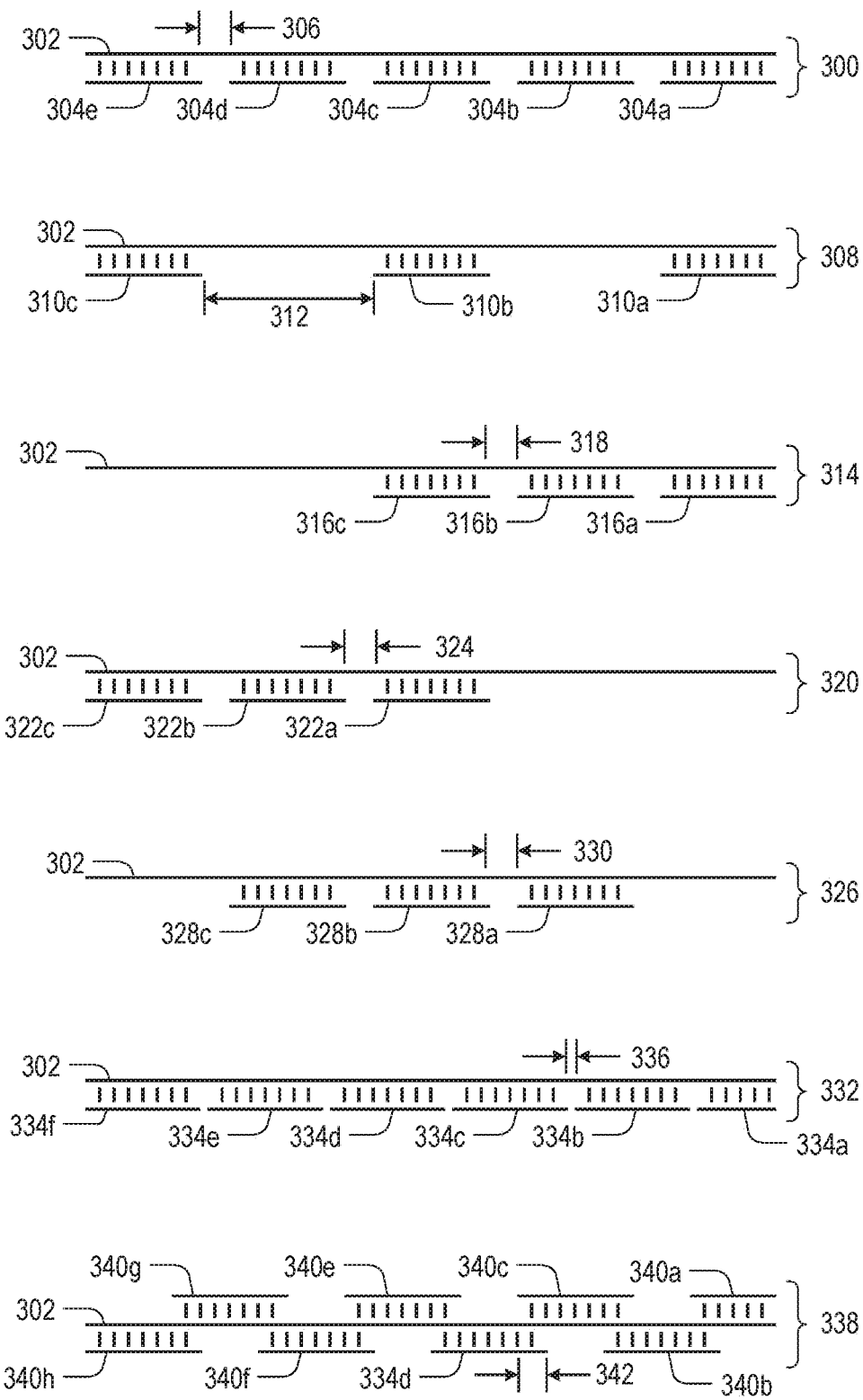
FIG. 3 is a schematic illustration of various embodiments of DNA probe designs for use with a system and method for depletion of target RNA transcripts from a nucleic acid sample according to the present disclosure.
Figure 4:
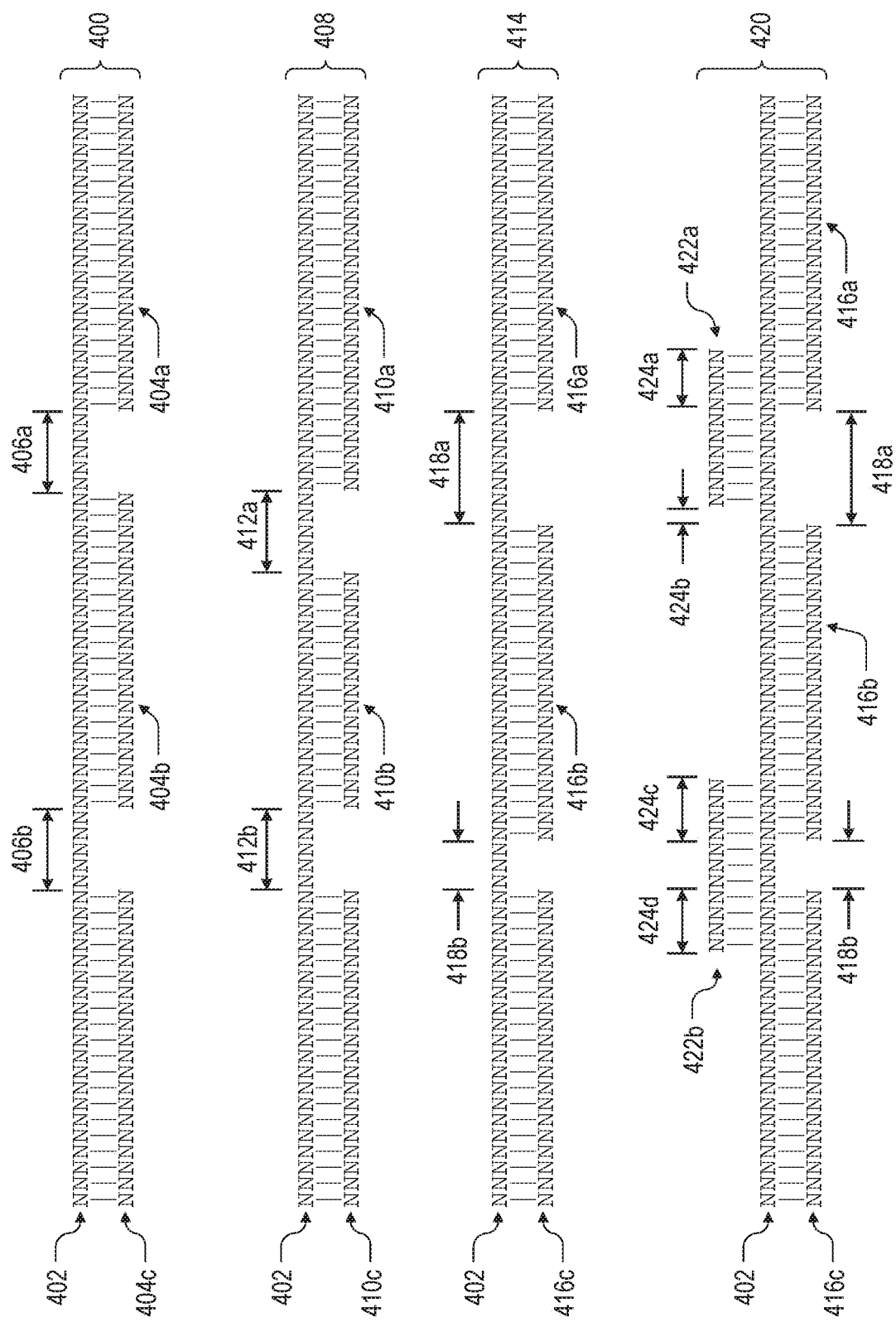
FIG. 4 is a schematic illustration of yet other embodiments of DNA probe designs for use with a system and method for depletion of target RNA transcripts from a nucleic acid sample according to the present disclosure. N is used to represent any nucleotide, and vertical lines extending between nucleotides are used to represent base pairing.

Turning now to FIGS. 3 and 4, DNA probes can be designed in a variety of ways according to the present disclosure. Previous approaches for depletion of rRNA have relied on only a small total number of DNA probes to target only a small total number of RNA transcripts. For example, one published approach for depleting human rRNA uses a total of only two DNA probes to target hemoglobin alpha (HBA) and hemoglobin beta (HBB) m RNAs while leaving all other RNA transcripts in the treated nucleic acid sample untargeted (Wu et al., 2007. Affymetrix Technical Note. *Globin reduction protocol: A method for processing whole blood RNA samples for improved array results*). Further, the approach relies on two twenty-three nucleotide long DNA probes, with each probe designed to target an approximately four-hundred and twenty (420) nucleotide long RNA transcripts, thereby resulting in a DNA probe to target RNA transcript coverage ratio of about 23:420 or about 0.05:1. In contrast to the aforementioned approach, embodiments of the present disclosure relate to the use of at least two or more DNA probes per target RNA transcript. Yet other embodiments of the present disclosure provide for a relatively greater DNA probe to target RNA transcript coverage ratio as will be described herein.

As shown in FIG. 3, a first example heteroduplex 300 includes a target RNA transcript 302 hybridized with a first DNA probe 304*a*, a second DNA probe 304*b*, a third DNA probe 304*c*, a fourth DNA probe 304*d*, and a fifth DNA probe 304*e* (collectively. "DNA probes 304"). Each of the target RNA transcripts 302 in FIG. 3 are illustrated from left to right in the 5' to 3' direction. Base-pairing between the target RNA transcript 302 and the DNA probes 304 is schematically illustrated by short vertical lines extending between the target RNA transcript 302 and a complementary portion of the corresponding one of the DNA probes 304 hybridized thereto. In one aspect, the DNA probes 304 can have a length of from about 10 nucleotides to about 150 nucleotides. In another aspect, the DNA probes 304 can have a length of from about 20 nucleotides to about 100 nucleotides. In yet another aspect, the DNA probes 304 can have a length of from about 25 nucleotides to about 50 nucleotides. In yet another aspect; the DNA probes 304 can have a length of from about 30 nucleotides to about 40 nucleotides.

Each of the DNA probes 304 can have a different nucleotide sequence designed to have up to 100% complementary to the indicated region or section of the target RNA transcript 302. In general, DNA probes will be designed to have 100% complementarity to the sequence of a section of a target RNA transcript. However, it may be useful to include one or more degenerate bases or intentional mismatches in a DNA probe. In one aspect, the use of a degenerate base in a DNA probe design can account for the presence of observed or predicted polymorphisms. It will also be appreciated that errors can occur during synthesis of DNA probes that result in insertions, deletions, or substitutions yielding DNA probes with less than 100% complementarity to a target RNA transcript.

As shown for the heteroduplex 300, the DNA probes 304 are designed to be spaced or tiled along the entire length of the target RNA transcript 302. While the DNA probes are illustrated as being spaced along the entire length of the target RNA transcript 302, FIG. 3 further illustrates that neither is there a single DNA probe 304 that extends along the full length of the target RNA transcript 302, nor are the DNA probes 304 necessarily spaced in a continuous manner. In particular, the DNA probes 304 are spaced discontinuously along the length of the target RNA transcript 302 such that there exist one or more unpaired nucleotides (on the target RNA transcript 302) located between portions of the target RNA transcript 302 that are hybridized with the DNA probes 304. The nucleotide spacing between DNA probes (Indicated at 306) can be between about one nucleotide and ten nucleotides and can be constant or variable along the length of the target RNA transcript 302. For example, the spacing of the DNA probes 304 along the target RNA transcript 302 is illustrated as being constant (i.e., there are a fixed number of unpaired target RNA transcript 302 bases between each of the hybridized DNA probes 304).

Although one example of DNA probe design is shown for the target RNA transcript 302, yet other DNA probes designs are possible according to the present disclosure. For example, a heteroduplex 308 including the same target RNA transcript 302 from the heteroduplex 300, a first DNA probe 310*a*, a second DNA probe 310*b*, and a third DNA probe 310*c* (collectively, "DNA probes 310") is illustrated as having a relatively greater nucleotide spacing between DNA probes (indicated at 312) as compared with the heteroduplex 300. The DNA probes 310 can be about the same length as the DNA probes 304 with at least one difference being that the spacing 312 is much greater than the spacing 306. For example, the DNA probes 310 can be designed to have a spacing 312 of between about eleven nucleotides and about one hundred nucleotides or more. Notably, the DNA probes 310 are still distributed across the entire length of the target RNA transcript 302, with the first DNA probe 310*a* and the third DNA probe 310*c* positioned at opposing ends of the target RNA transcript 302, and the second DNA probe 310*b* positioned at an intermediate point between the first DNA probe 310*a* and the third DNA probe 310*c*. In one aspect, it may not be necessary to design probes for complete coverage of a given target RNA transcript as shown for the heteroduplex 308, as the use of a relatively fewer number of DNA probes with increased spacing between each of the probes may be sufficient to deplete the target RNA transcript. For example, it may be useful to generate degraded target RNA transcript fragments (i.e., following hybridization and treatment with an RNase enzyme) that are less than about 50 nucleotides. Thereafter, a size-based separation step can be used to recover untargeted RNA transcripts that have an average nucleotide length that is greater than the average nucleotide length of the RNA fragments resulting from the degraded target RNA transcript.

In comparison to the heteroduplex 308, a heteroduplex 314 illustrates yet another DNA probe design approach that includes the target RNA transcript 302, a first DNA probe 316*a*, a second DNA probe 316*b*, and a third DNA probe 316*c* (collectively, "DNA probes 316"). For the heteroduplex 314, the DNA probes 316 are each positioned at the 3' end of the target RNA transcript 302 with a spacing 318 between each of the probes comparable to the spacing 306. In contrast to the DNA probe design for either of the heteroduplex 300 and the heteroduplex 308, none of the DNA probes 316 are designed to hybridize to the 5' end of the RNA transcript 302. In a related example, a heteroduplex 320 includes the target RNA transcript 302, a first DNA probe 322*a*, a second DNA probe 322*b*, and a third DNA probe 322*c* (collectively, "DNA probes 322). The DNA probes 322 are each positioned at the 5' end of the target RNA transcript 302 with a spacing 324 between each of the probes comparable to the spacing 306 or the spacing 318. In contrast to both the heteroduplex 314 and either of the heteroduplex 300 and the heteroduplex 308, none of the DNA probes 322 are designed to hybridize to the 3' end of the RNA transcript 302. Finally, a third example of DNA probe design characterized at least in part by incomplete target RNA transcript coverage includes a heteroduplex 326. The DNA probe design for hybridizing the target RNA transcript 302 in the heteroduplex 326 omits DNA probe coverage at the 5' and 3' termini of the target RNA transcript 302, but does include a first DNA probe 328*a*, a second DNA probe 328*b*, and a third DNA probe 328*c* (collectively, "DNA probes 328"), where the DNA probes 328 are each designed to hybridize to a portion at an intermediate point between the 5' and 3' ends of the target RNA transcript 302. A spacing 330 of the DNA probes 328 can be relative small, similar to the spacing 306, for example.

For a variety of reasons, it can be useful to omit DNA probes for hybridization to either of the 5' end of an RNA transcript the 3' end of an RNA transcript or a combination thereof. In one aspect, the use of fewer DNA probes can provide for a simpler overall design, thereby reducing off-target effects (e.g. undesirable probe hybridization with untargeted RNA transcripts), decreasing manufacturing costs, and the like. Moreover the use of DNA probes that hybridize to only a portion of a given RNA transcript can provide sufficiently degraded target RNA transcript depending on the overall length or complexity of the target RNA transcript. In another aspect depending on the downstream analysis or sequencing methods employed, degrading either the interior portion or one or both ends of a given target RNA transcript can be sufficient to effectively prevent downstream conversion to cDNA or amplification of the RNA. Yet other factors can also motivate a probe design including incomplete target RNA transcript coverage.

With continued reference to FIG. 3, two further examples of DNA probe design for targeted depletion include the use of closely spaced or overlapping DNA probes. In a first example, a heteroduplex 332 includes the target RNA transcript 302, a first DNA probe 334a, a second DNA probe 334b, a third DNA probe 334c, a fourth DNA probe 334d, a fifth DNA probe 334e, and a sixth DNA probe 334f (collectively, "DNA probes 334"), where the DNA probes 334 are designed to hybridize along the length of the target RNA transcript 302 with a spacing 336 of between zero and about two nucleotides. In the present example of the heteroduplex 332, there is the possibility for every nucleotide in the target RNA transcript to be hybridized by one (and only one) of the DNA probes (as the DNA probes do not overlap). However, there are still multiple DNA probes used to provide the illustrated coverage of the target RNA transcript 302 in the heteroduplex 332, as opposed to the use of a single continuous DNA probe.

In a second example of closely spaced or overlapping DNA probe sequences, a heteroduplex 338 includes the target RNA transcript 302, a first DNA probe 340a, a second DNA probe 340b, a third DNA probe 340c, a fourth DNA probe 340d, a fifth DNA probe 340e, a sixth DNA probe 340f, a seventh DNA probe 340g, and an eighth DNA probe 340h (collectively, "DNA probes 334"), where the DNA probes 340 are designed to hybridize along the length of the target RNA transcript 302 with an overlap 342 of at least one nucleotide. The overlap 342 results from a probe design where the 3' end of one DNA probe has the potential to hybridize to the same portion of a target RNA transcript as 5' end of another DNA probe. For example, the 3' end of the first DNA probe 340a is designed to be capable of hybridizing to the same portion of the target RNA transcript 302 as the 5' end of the second DNA probe 340b. Notably, each of the 3' end of the first DNA probe 340a and the 5' end of the second DNA probe 340b can simultaneously hybridize to the same portion of the target RNA transcript 302. However, it can still be useful to select a probe design including overlapping DNA probes. In one aspect, the DNA probes can hybridize sequentially to an individual target RNA transcript during a treatment step. In another aspect; the DNA probes can hybridize simultaneously to different copies of the same target RNA transcript. Yet other design considerations can additionally or alternatively suggest the use of overlapping DNA probes for hybridization to a target RNA transcript.

With reference to FIG. 4, and as described with reference to FIG. 3, DNA probes can be designed in a variety of ways. In one aspect, it can be generally useful to design two or more probes for hybridization to the same target RNA transcript. However, the characteristics of the probe design can vary greatly. In one aspect, a heteroduplex 400 includes a target RNA transcript 402, a first DNA probe 404a, a second DNA probe 404b, and a third DNA probe 404c (collectively, "DNA probes 404"). Each of the DNA probes 404 have an each length of twenty nucleotides. Moreover, each of the DNA probes 404 is designed to hybridize with a uniform spacing along the length of the target RNA transcript 402. As illustrated for the heteroduplex 400, a spacing 406a between adjacent ends of the first DNA probe 404a and the second DNA probe 404b is equal to the spacing 406b between adjacent ends of the second DNA probe 404b and the third DNA probe 404c. While the spacing 406a and the spacing 406b are illustrated as five nucleotides, it will be appreciated that a larger or smaller nucleotide spacing can be used. In another aspect, additional or alternative probes designs, including variable DNA probe lengths and inter-DNA probe spacing, can be used. For example, the heteroduplex 408 includes the target RNA transcript 402 and three alternative DNA probes designed for hybridization thereto. In one aspect a first DNA probe 410a has a length of twenty-five nucleotides, a second DNA probe 410b has a length of fifteen nucleotides, and a third DNA probe 410c has a length of twenty nucleotides (collectively, "DNA probes 410"). The DNA probes 410 have a variable length design as compared to the DNA probes 404. However, akin to the spacing 406 for the heteroduplex 400, a five nucleotide spacing 412a between adjacent ends of the first DNA probe 410a and the second DNA probe 410b is equal to a spacing 412b between adjacent ends of the second DNA probe 410b and the third DNA probe 410c. Accordingly, in some DNA probes designs, the DNA probe length can be varied while maintaining a uniform spacing between adjacent DNA probes.

In yet another example of DNA probe design, a heteroduplex 414 includes the target RNA transcript 402, a first DNA probe 416a, a second DNA probe 416b, and a third DNA probe 416c (collectively, "DNA probes 416"). By way of comparison to either of the heteroduplex 400 and the heteroduplex 408, the DNA probes 416 in the heteroduplex 414 are each twenty nucleotides in length with a variable spacing between each of the adjacent probes. In one aspect, a spacing 418a is seven nucleotides, whereas a spacing 418b is only three nucleotides. The spacing for a given probe design can therefore vary between pairs of adjacent probes without necessarily varying the length of each of the DNA probes. However, as shown for a heteroduplex 420 in FIG. 4, in some embodiments, each of the DNA probe length and the spacing between adjacent DNA probes can vary simultaneously. In the illustrated example of the heteroduplex 420, the target RNA transcript 402 is capable of hybridization to the DNA probes 416 as well as a first DNA probe 422a and a second DNA probe 422b (collectively, "DNA probes 422"). In one aspect, the first DNA probe 422a has a length of ten nucleotides and is designed in part to be capable of hybridization to the same portion of the target RNA transcript 420 as the first DNA probe 416a with an overlap 424a of four nucleotides. Further, the 5' end of the DNA probe 422b exhibits an overlap 424c of four nucleotides with the adjacent DNA probe 416b, while the 3' end of the DNA probe 422b exhibits an overlap 424d of four nucleotides with the adjacent DNA probe 416c.

As discussed with respect to the heteroduplex 338 in FIG. 3, the DNA probe 416a and the DNA probe 422a will not necessarily be able to hybridize simultaneously to the target RNA transcript 402. Similarly, the DNA probe 422b and either of the DNA probe 416b and the DNA probe 416c will not necessarily be able to hybridize simultaneously to the target RNA transcript 402. Still, it can be useful to provide a design including overlapping DNA probe sequences as illustrated for the heteroduplex 420 in FIG. 4. However, both ends of a given DNA probe need not include overlapping sequence with an adjacently hybridizable DNA probe. For example, in contrast to the overlap 424a exhibited at the 5' end of the DNA probe 422a, the 3' end of the DNA probe 422a is spaced apart from the 5' end of the DNA probe 416b with a spacing 424b of one nucleotide. It will also be appreciated that further combinations of DNA probe length and spacing are also encompassed by embodiments of the present disclosure.

Figure 5:
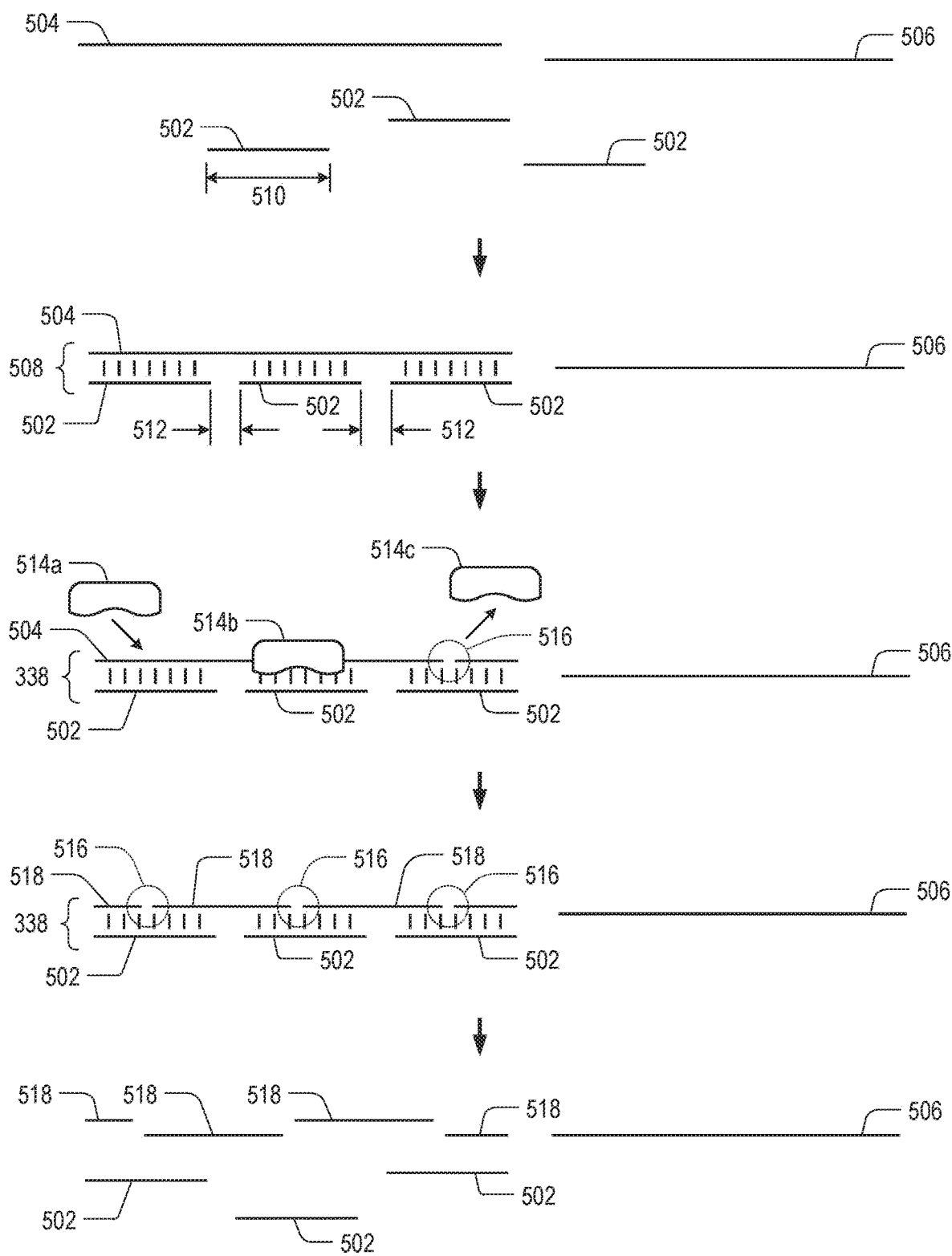
FIG. 5 is a schematic illustration detailing an embodiment of a method for depletion of target RNA transcripts from a nucleic acid sample according to the present disclosure.

Referring now to FIG. 5, an overview of a method for depleting target nucleic acids from a nucleic acid sample according to the present disclosure includes a combining a plurality of DNA probes 502 with a nucleic acid sample including a plurality of target RNA transcripts 504 and a plurality of non-target (or untargeted) RNA transcripts 506. While FIG. 5 shows only a single target RNA transcript 504 an untargeted RNA transcript 506 for simplicity, a nucleic acid sample will include at least three unique target RNA transcripts. In another aspect a nucleic acid sample will include at least ten unique target RNA transcripts. In yet another aspect, a nucleic acid sample will include at least one hundred unique target RNA transcripts.

The DNA probes 502 are each hybridizable with a corresponding one of the target RNA transcripts 504 to form one or more DNA-RNA heteroduplexes 508. By contrast, the untargeted RNA transcripts 506 are preferably not hybridized by any of the DNA probes 502. Depending on the design of the DNA probes 502 for depleting the target RNA transcripts 504, the nucleotide length 510 of the DNA probes 502 and the spacing 512 between adjacently hybridized DNA probes 502 can vary. In one aspect; the DNA probes 502 are hybridizable along the length of each of the target RNA transcripts 504 with a regular spacing 512, where for each pair of adjacently hybridizable DNA probes 502, the 3' end of a first one of the pair of DNA probes 502 is spaced apart from the 5' end of a second one of the pair of DNA probes 502 by a nucleotide interval relative to the target RNA transcript 504 that is less than about fifty nucleotides. In another example, the interval between adjacently hybridizable DNA probes 502 is less than about ten nucleotides, in yet another example, the interval between adjacently hybridizable DNA probes 502 is less than about five nucleotides.

The number of different DNA probes 502 designed to hybridize with each unique one of the target RNA transcripts 504 can additionally (or alternatively) be variable. In FIG. 5, for example, at least three different DNA probes 502 are hybridizable to the target RNA transcript 504. In other embodiments, the number of unique DNA probes 502 hybridizable to a unique target RNA transcript 504 is at least ten. In a further aspect, the fraction of the total number of bases of each target RNA transcript 504 hybridizable by the DNA probes 502 is at least 0.5. That is, the fraction of the number of nucleotides in the target RNA transcript that are capable of base pairing with a DNA probe designed to hybridize to the target RNA transcript is at least 0.5. In another aspect, the fraction of the total number of bases of the target RNA transcript 504 hybridizable by the DNA probes 502 is at least 0.75. In yet another aspect; the fraction of the total number of bases of the target RNA transcript 504 hybridizable by the DNA probes 502 is at least 0.9.

The heteroduplexes 508 can be treated in order to deplete the nucleic acid sample of the target RNA transcripts 504. In the present example shown in FIG. 5, the heteroduplexes 508 are treated with an enzyme 514 having RNA-DNA hybrid ribonucleotidohydrolase activity. One example of an enzyme having RNA-DNA hybrid ribonucleotidohydrolase activity is RNase H (EC 3.1.26.4), although any enzyme possessing RNA-DNA hybrid ribonucleotidohydrolase activity can be used. In a first step, an unbound one of the enzymes 514a identifies a portion of the heteroduplex 508 including one of the DNA probes 502 hybridized to a portion of the corresponding target RNA transcript 504 to become a bound enzyme 514b. The bound enzymes 514b then interacts with the heteroduplex 508 to at least partially degrade a portion of the target RNA transcript 504. Upon disassociation, the bound enzyme 514b becomes a newly unbound enzyme 514c, revealing that the target RNA transcript 504 portion of the heteroduplex 508 now includes a nick or cut-site 516 that subdivides the target RNA transcript 504 into two separate target RNA fragments 518. In particular, the enzymes 514 preferably cut or otherwise degrade the target RNA transcript 504 at two or more locations, thereby generating a plurality of cut-sites 516. Upon disassociation of the DNA probes 502 from the treated target RNA transcript 504 (e.g., through heating, enzymatic digestion of the DNA fragments, or another like dissociation process), the nucleic acid sample will include a plurality of target RNA fragments 518 resulting from the (now depleted) target RNA transcripts 504, along with intact untargeted RNA transcripts 506. The untargeted RNA transcripts 506 can then be purified away from the target RNA fragments 518 and DNA probes 502 to enable downstream sequencing or other like analysis.

With respect to downstream analysis of the nucleic acid sample, it can be useful to determine the extent to which one or more of the target RNA transcripts 504 were depleted. One method for measuring depletion includes quantifying the number of fragments per kilobase of transcript per million mapped reads (FPKM) for each of the target RNA transcripts following sequencing of the depleted nucleic acid sample (Equation 1).

$$FPKM_i = \frac{X_i}{\tilde{l}_i N} \cdot 10^9 \quad \text{(Eq. 1)}$$

In Equation 1, $FPKM_i$ is the FPKM of a given RNA transcript (or fragment thereof) i, $X_i$ is the counts observed for the transcript i, $\tilde{l}_i$ is the effective length of the RNA transcript i (computed as 1 plus the actual length less the mean of the fragment length distribution learned from the aligned read for the sequencing experiment), and N is the number of fragments sequenced. The FPKM for a target RNA transcript from an untreated (control) sample (I.e., a sample where the target RNA transcript was purposely not depleted) is compared with the FPKM for the same target RNA transcript from a treated sample (i.e., a sample where the target RNA transcript was purposely depleted as illustrated in FIG. 5). The ratio of the FPKM for the target RNA transcript from the treated sample to the FPKM for the target RNA transcript from the untreated (control) sample can be used to determine a percent depletion (Equation 2). Notably, the FPKM of a given RNA transcript in the treated sample should be less than or equal to the FPKM of the same transcript in the treated sample when using Equation 2.

$$\% \text{ depletion} = \left(1 - \frac{FPKM_{i,treated}}{FPKM_{i,untreated}}\right) \cdot 100\% \quad \text{(Eq. 2)}$$

In one aspect, a method according to the present disclosure can be employed to deplete the quantity of each of the target RNA transcript by at least about 50% (i.e., 50% depletion as determined with Equation 2). In another aspect, a method according to the present disclosure can be employed to deplete the quantity of each of the target RNA transcript by at least about 80%. In yet another aspect, a method according to the present disclosure can be employed to deplete the quantity of each of the target RNA transcript by at least about 90%. In still another aspect, a method according to the present disclosure can be employed to deplete the quantity of each of the target RNA transcript by at least an order of magnitude as compared with an untreated (control) sample.

In some embodiments, the methods described herein and illustrated at least in FIG. 5 can be at least partially facilitated through the use of a kit according to the present disclosure. One example of a kit for depleting target nucleic acids from a nucleic acid sample includes a plurality of DNA probes. Each of the DNA probes is hybridizable to form a heteroduplex with at least one of a plurality of target RNA transcripts in a nucleic acid sample. The DNA probes can be custom designed based on the known or suspected sequences of RNA transcripts included in the nucleic acid sample. In one aspect, the DNA probes can be designed to hybridize or target at least three unique target RNA transcripts. However, the number of unique target RNA transcripts hybridized by the DNA probes can be at least ten or more. For example, in some embodiments, a kit can include a plurality of DNA probes for hybridizing to, and ultimately depleting, at least one hundred unique target RNA transcripts. The kit can further include an enzyme having RNA-DNA hybrid ribonucleotidohydrolase activity. In one particular embodiment, a kit for depleting target nucleic acids from a nucleic acid sample includes a plurality of DNA probes for hybridization to the top ten most highly expressed genes in a nucleic acid sample. In one aspect, the number of DNA probes designed to target each unique RNA transcript for each of the top ten most highly expressed genes is at least three. In another aspect the kit can include RNase H or another enzyme having RNA-DNA hybrid ribonucleotidohydrolase activity. In yet another aspect, the kit can include any additional materials useful for processing the nucleic acid sample including, but not limited to buffers, DNA polymerase, reverse transcriptase, RNase A, DNase 1, nuclease-free water, sequencing adapters, primers for amplification or sequencing, the like, and combinations thereof.

EXAMPLES

Figure 6:
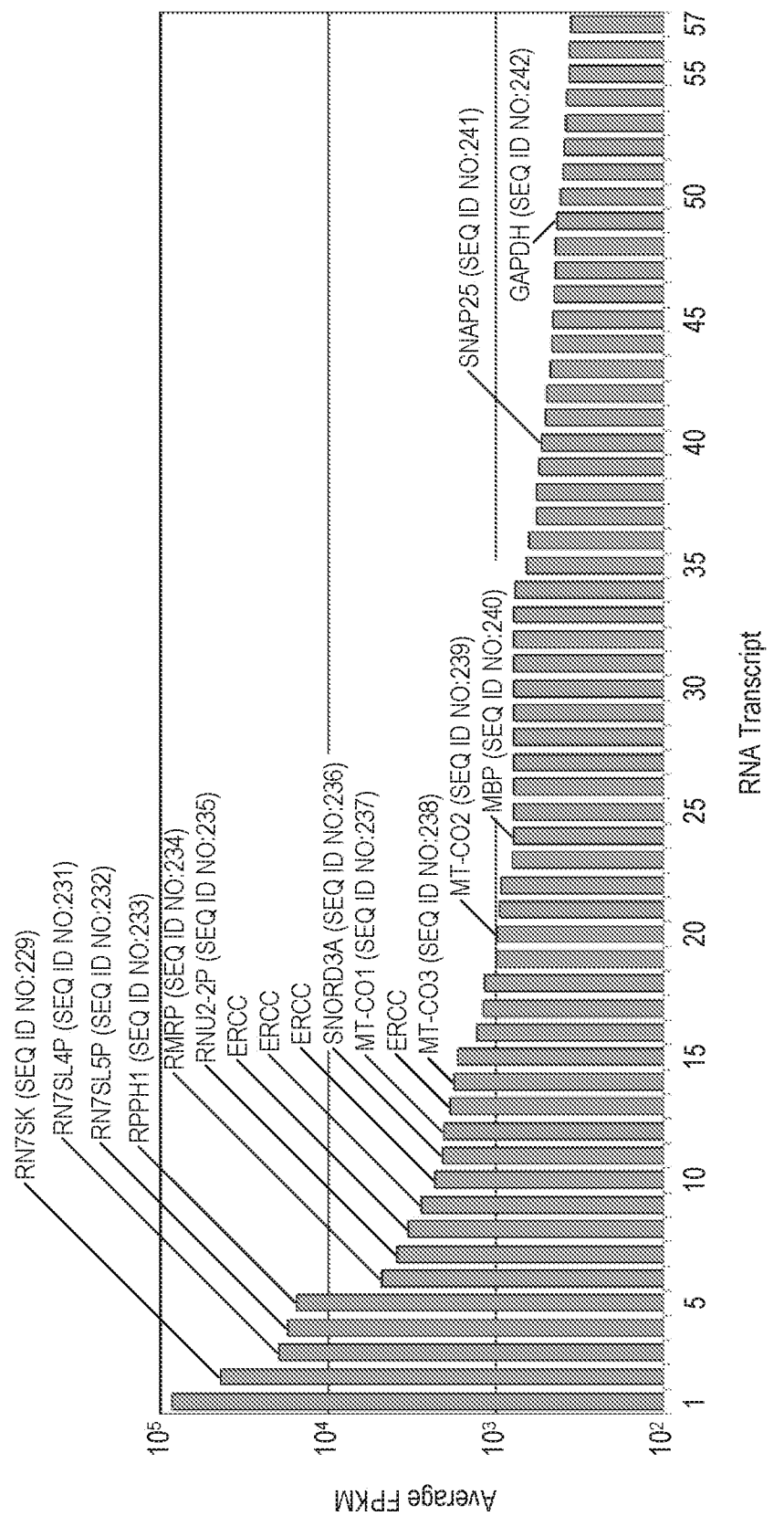
FIG. 6 is a plot of average FPKM values for the most abundant RNA transcripts from human brain total RNA as determined by sequencing. Four RNA-Seq experiments were performed with human brain total RNA. FPKM values were calculated and the most abundant transcripts were identified from each of the four experiments and plotted in order of descending average FPKM value. Data corresponding to RNA transcripts targeted for depletion in subsequent experiments are denoted along with data corresponding to ERCC spike-in controls (ERCC). Of the 57 data points shown, the 14 RNA transcripts selected for depletion were RN7SL1 (SEQ ID NO:229) (1), RN7SK (SEQ ID NO:230) (2), RN7SL4P (SEQ ID NO:231) (3). RN7SLSP (SEQ ID NO:232) (4), RPPH.1 (SEQ ID NO:233) (5), RMRP (SEQ ID NO:234) (6), RNU2-2P (SEQ ID NO:235) (7), SNORD3A (SEQ ID NO:236) (11), MT-CO1 (SEQ ID NO:237) (12). MT-CO3 (SEQ ID NO:238) (14), MT-CO2 (SEQ ID NO:239) (20), MBP (SEQ ID NO:240) (24). SNAP25 (SEQ ID NO:241) (40), and GAPDH (SEQ ID NO:242) (49).

For Identification of depletion targets, four RNA-Seq experiments were performed using 100 ng human brain total RNA (AMBION). Sequencing libraries (cDNA) were constructed using the KAPA Stranded RNA-Seq Kits with RiboErase (KAPA BIOSYSTEMS) according to manufacturer instructions. The cDNA libraries were sequenced using a HiSeq 2500 System sequencing instrument (ILLUMINA) with 2×100 bp reads. The raw sequencing reads were randomly down-sampled to a total of 3 million reads and the data were analyzed using standard bioinformatics methods. FPKM were calculated and the top 50 highest expressing transcripts were identified from each of the four experiments. The data from the top 50 transcripts identified in all four experiments, were combined and the average FPKM values were calculated (FIG. 6).

The top ten highest expressing transcripts, were initially targeted for depletion. Since three of these top ten transcripts were very similar in sequence and could be targeted by several of the same depletion oligos (i.e., DNA probes), an additional three gene transcripts were targeted for depletion. The coding DNA (cDNA) sequences of each of the fourteen targeted genes (i.e., gene transcripts) targeted for depletion in descending order of average FPKM values were: RN7SL1 (NR 002715.1) (SEQ ID NO:229), RN7SK (NR_001445.2) (SEQ ID NO:230), RN7SL4P (NG_002425.3) (SEQ ID NO:231), RN7SLSP (NG_002426.2) (SEQ ID NO:232), RPPH1 (HG505981.1) (SEQ ID NO:233), RMRP (NR_003051.3) (SEQ ID NO:234), RNU2-2P (NG_044735.1) (SEQ ID NO:235), SNORD3A (HG508764.1) (SEQ ID NO:236), MT-CO1 (ENST00000361624) (SEQ ID NO:237), MT-CO3 (ENST0000362079) (SEQ ID NO:238), MT-CO2 (ENST00000361739) (SEQ ID NO:239), MBP (NM_001025081.1) (SEQ ID NO:240), SNAP2S (NM_1308112) (SEQ ID NO:241), and GAPDH (NM_001289745.1) (SEQ ID NO:242). The fourteen genes targeted for depletion in the various examples, including expression abundance rank (most abundant=1), average FPKM value, and RNA transcript length in nucleotides (nt), are listed in Table 1.

TABLE 1

| Target # | Gene ID | Rank | Average FPKM | RNA transcript length (nt) |
| --- | --- | --- | --- | --- |
| 1 | RN7SL1 (SEQ ID NO: 229) | 1 | 86128 | 299 |
| 2 | RN7SK (SEQ ID NO: 230) | 2 | 44167 | 332 |
| 3 | RN7SL4P (SEQ ID NO: 231) | 3 | 19646 | 295 |
| 4 | RN7SL5P (SEQ ID NO: 232) | 4 | 17515 | 321 |
| 5 | RPPH1 (SEQ ID NO: 233) | 5 | 15597 | 333 |
| 6 | RMRP (SEQ ID NO: 234) | 6 | 4834 | 277 |
| 7 | RNU2-2P (SEQ ID NO: 235) | 7 | 3879 | 191 |
| 8 | SNORD3A (SEQ ID NO: 236) | 8 | 2086 | 699 |
| 9 | MT-CO1 (SEQ ID NO: 237) | 9 | 2066 | 1542 |
| 10 | MT-CO3 (SEQ ID NO: 238) | 10 | 1776 | 784 |
| 11 | MT-CO2 (SEQ ID NO: 239) | 16 | 988 | 684 |
| 12 | MBP (SEQ ID NO: 240) | 18 | 790 | 2254 |
| 13 | SNAP25 (SEQ ID NO: 241) | 33 | 531 | 2069 |
| 14 | GAPDH (SEQ ID NO: 242) | 40 | 439 | 1490 |

For design of the DNA probes for targeted depletion, the sequences of the targeted transcripts were retrieved from the National Center for Biotechnology Information (NCBI) and Ensembl (release 83) databases, DNA probes were designed as DNA sequences of uniform length (35 nucleotides in length for all genes except GAPDH (SEQ ID NO:242) for which the oligos were 38 nucleotides in length), complementary to the sequences of the targeted RNA transcripts. Further, the DNA probes for depletion of GAPDH (SEQ ID NO:242) included a 3' inverted dT chemical modification, whereas DNA probes for depletion of the other target RNA transcripts were not modified. The spacing between the 3' end of one depletion oligo and the 5' end of the adjacent depletion oligo was varied, for example, from about two nucleotides (GAPDH (SEQ ID NO:242)) to about ten nucleotides (MBP (SEQ ID NO:240)), but was generally uniform for DNA probes designed for depletion of a unique target RNA transcript (Table 2):

TABLE 2

| Gene ID | No. DNA probes | probe length (nt) | typical spacing (nt) | coverage (%) |
|---|---|---|---|---|
| RN7SL1 (SEQ ID NO: 229) | 7 | 35 | 5 | 81.9 |
| RN7SK (SEQ ID NO: 230) | 7 | 35 | 5 | 73.8 |
| RN7SL4P (SEQ ID NO: 231) | 7 | 35 | 5 | 83.1 |
| RN7SL5P (SEQ ID NO: 232) | 7 | 35 | 5 | 76.3 |
| RPPH1 (SEQ ID NO: 233) | 8 | 35 | 5 | 84.1 |
| RMRP (SEQ ID NO: 234) | 6 | 35 | 5 | 75.8 |
| RNU2-2P (SEQ ID NO: 235) | 4 | 35 | 5 | 73.3 |
| SNORD3A (SEQ ID NO: 236) | 16 | 35 | 5 | 80.1 |
| MT-CO1 (SEQ ID NO: 237) | 34 | 35 | 10 | 77.2 |
| MT-CO3 (SEQ ID NO: 238) | 17 | 35 | 10 | 75.9 |
| MT-CO2 (SEQ ID NO: 239) | 15 | 35 | 10 | 76.8 |
| MBP (SEQ ID NO: 240) | 50 | 35 | 10 | 76.1 |
| SNAP25 (SEQ ID NO: 241) | 25 | 35 | 10 | 42.3 |
| GAPDH (SEQ ID NO: 242) | 37 | 38 | 2 | 92.9 |

In general, the starting approach for the DNA probe designs in Table 2 was to maintain consistent DNA probe length and DNA probe spacing. However, based on factors such as the sequence and length of a particular target RNA transcript, the actual spacing between DNA probes was varied for several of the DNA probe designs including those DNA probes targeting SNAP25 (SEQ ID NO:241), RN7SK (SEQ ID NO:230), and RNU2-2P (SEQ ID NO:235). Sequences for the DNA probes described in Table 2 were as follows: GAPDH probes (SEQ ID NOs:1-37); MBP probes (SEQ ID NOs:38-87); MT-CO1 probes (SEQ ID NOs:88-121); MT-CO2 probes (SEQ ID NOs:122-136); MT-CO3 probes (SEQ ID NOs:137-153); RMRP probes (SEQ ID NOs:154-159); RN7SL1 probes (SEQ ID NOs:160-168); RN7SLSP probes (SEQ ID NOs:160-168); RN7SL4P probes (SEQ ID NOs:160-168); RN7SK probes (SEQ ID NOs:169-175); RNU2-2P probes (SEQ ID NOs:176-179); RPPH1 probes (SEQ ID NOs:180-187); SNAP2S probes (SEQ ID NOs:188-212); and SNORD3A probes (SEQ ID NOs:213-228).

The indicated percent coverage for each set of DNA probes was determined by summing the DNA probe length for each of the DNA probes targeting a given RNA transcript and dividing by the RNA transcript length (Equation 3).

$$\% \text{ coverage} = \frac{\sum_i (\text{probe length})_i}{RNA \text{ transcript length}} \cdot 100\% \quad (\text{Eq. 3})$$

where i represents the number of different DNA probes designed to hybridize to a unique target RNA transcript.

Targeted depletion of rRNA in conjunction with a single additional target RNA transcript was first demonstrated for a human total RNA sample. In general, the experiment followed the protocol outlined in the KAPA Stranded RNA-Seq Kit with RiboErase (HMR) (KR1151-v3.15; KAPA BIOSYSTEMS), with changes to the protocol noted as follows: Human Cervical Adenocarcinoma (HeLa-S3) Total RNA at a concentration of 1 mg/mL (AMBION) was selected as the nucleic acid sample for targeted depletion. Thirty-seven DNA probes were designed against glyceraldehyde-3-phosphate dehydrogenase (GAPDH) using transcript variant 3 of GAPDH (NM_001289745.1) (SEQ ID NO:242) as a reference (Table 2). The DNA probes were resuspended in nuclease free water to a concentration of 10 uM and a dilution series was made to achieve a range of molar ratios between 0.0001:1, and 1.000:1 DNA probe to target RNA transcript (DNA:RNA ratio) for an input of 10 μg total RNA (Table 3; n. a.=not applicable).

TABLE 3

| sample | DNA:RNA ratio |
|---|---|
| 0 | n.a. |
| 1 | 1000:1 |
| 2 | 100:1 |
| 3 | 10:1 |
| 4 | 1:1 |
| 5 | 0.1:1 |
| 6 | 0.01:1 |
| 7 | 0.001:1 |
| 8 | 0.0001:1 |

Depletion of GAPDH (SEQ ID NO:242) target RNA transcript with RNase H treatment was carried out in the presence of a GAPDH (SEQ ID NO:242) depletion oligos at the ratios indicated in Table 3. GAPDH (SEQ ID NO:242) depletion oligos were added at the same time as a RiboErase probes. Stranded RNA library preparation was carried out according to the KAPA Stranded RNA-Seq Kit with RiboErase (HMR) protocol. PCR amplification was carried out as described in Table 4.

TABLE 4

| Step | Temp (° C.) | Time (m:s) | Cycles |
|---|---|---|---|
| Initial Denaturation | 98 | 0:45 | 1 |
| Denaturation | 98 | 0:15 | |
| Annealing* | 60 | 0:30 | 10 |
| Extension | 72 | 0:30 | |
| Final Extension | 72 | 5:00 | 1 |
| Hold | 4 | n.a. | 1 |

Figure 7:
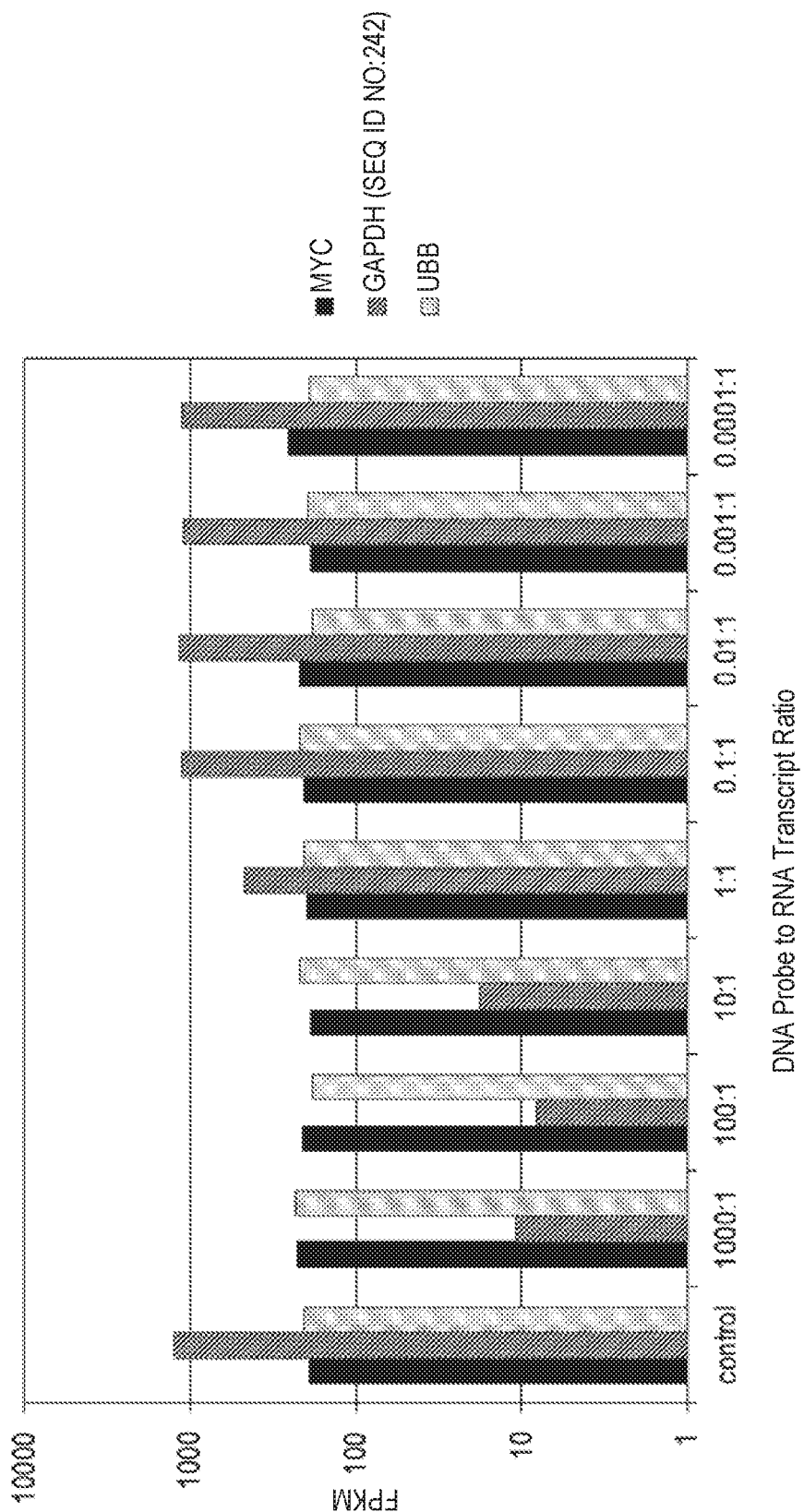
FIG. 7 is a plot of FPKM values for three unique RNA transcripts as a function of DNA probe to target RNA transcript ratio for nine separate depletion experiments, DNA probes designed for depletion of GAPDH (SEQ ID NO:242) target RNA transcripts were added to total RNA samples at a DNA probe to GAPDH (SEQ ID NO:242) target RNA transcript ratio of 1000:1, 100:1, 10:1, 1:1, 0.1:1, 0.01:1, 0.001:1, or 0.0001:1. Control data were collected for a total RNA sample with DNA probes targeting GAPDH (SEQ ID NO:242) omitted (control). The effect of DNA probe to GAPDH (SEQ ID NO:242) target RNA ratio on measured FPKM following depletion and sequencing was compared against untargeted RNA transcripts MYC and UBB.

The resulting amplified libraries were prepared using MiSeq V2 Reagent Kit (ILLUMINA) and sequenced on a MiSeq desktop sequencer (ILLUMINA). FPKM values were determined for each of the target RNA transcripts from the resulting sequencing data (Table 5; FIG. 7). FPKM values for MYC (X00364.2) and UBB (NM_018955.3) were used as internal controls for each sequenced nucleic acid sample.

TABLE 5

| sample | DNA:RNA ratio | MYC (FPKM) | GAPDH (SEQ ID NO: 242) (FPKM) | UBB (FPKM) | Depletion (%) |
|---|---|---|---|---|---|
| 0 | n.a. | 189.5 | 1273.7 | 207.9 | n.a. |
| 1 | 1000:1 | 229.0 | 11.0 | 232.5 | 99.1 |
| 2 | 100:1 | 212.1 | 8.2 | 183.2 | 99.4 |
| 3 | 10:1 | 187.7 | 17.9 | 220.4 | 98.6 |
| 4 | 1:1 | 196.7 | 478.0 | 207.2 | 62.5 |
| 5 | 0.1:1 | 206.0 | 1121.1 | 217.7 | 12.0 |
| 6 | 0.01:1 | 217.3 | 1163.5 | 183.0 | 8.7 |
| 7 | 0.001:1 | 187.7 | 1099.5 | 193.9 | 13.7 |
| 8 | 0.0001:1 | 254.0 | 1121.8 | 190.3 | 11.9 |

Figure 8:
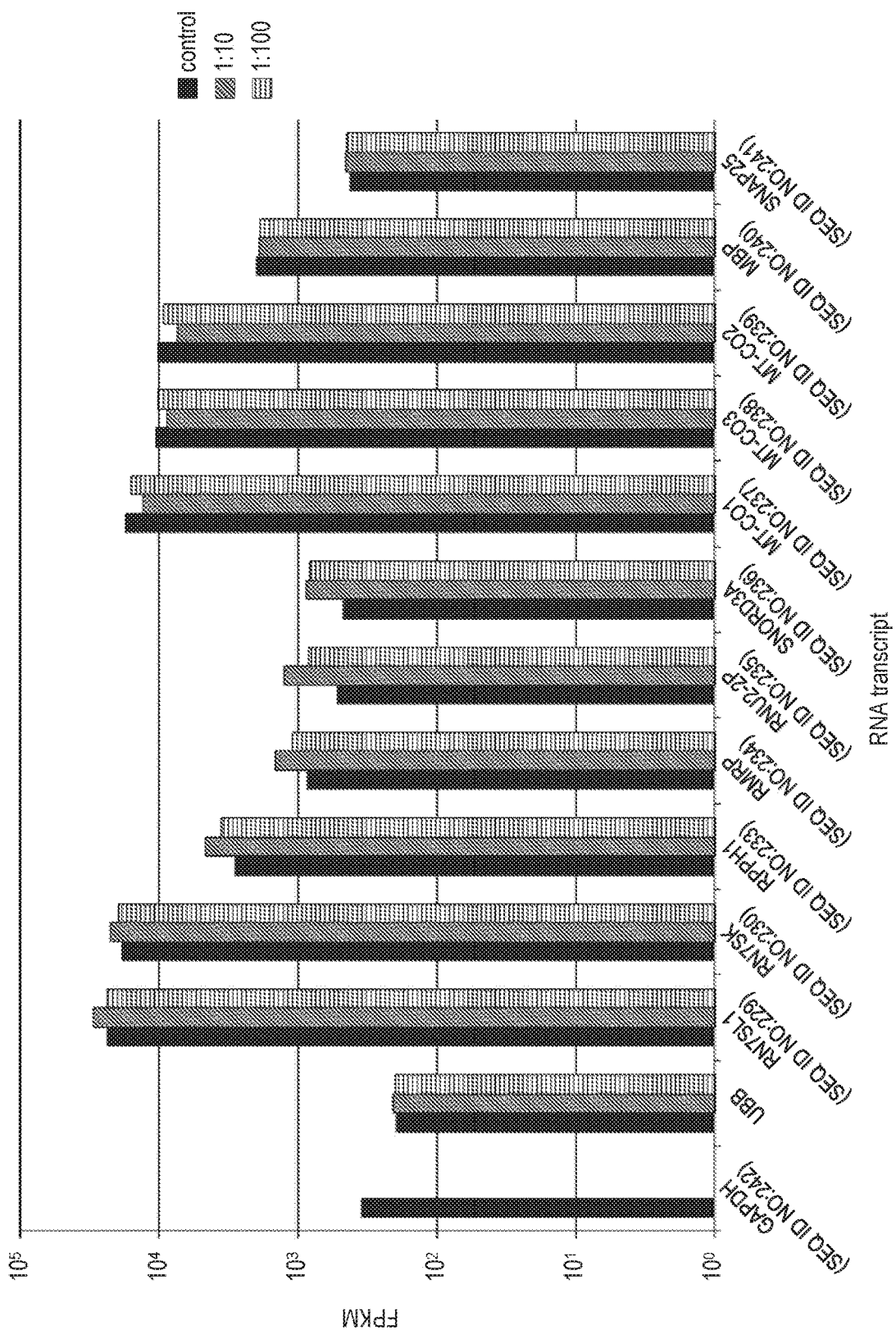
FIG. 8 is a plot of FPKM values for thirteen unique RNA transcripts as a function of DNA probe to target RNA transcript ratio for three separate depletion experiments. DNA probes designed for depletion of GAPDH (SEQ ID NO:242) target RNA transcripts were added to total RNA samples at a DNA probe to GAPDH (SEQ ID NO:242) target RNA transcript ratio of 1:10 or 1:100. Control data were collected for a total RNA sample with DNA probes targeting GAPDH (SEQ ID NO:242) omitted (control). The effect of DNA probe to GAPDH (SEQ ID NO:242) target RNA ratio on measured FPKM following depletion and sequencing was compared against a number of untargeted RNA transcripts including a selection of the most abundant RNA transcripts as shown in FIG. 6. Untargeted RNA transcripts compared against GAPDH (SEQ ID NO:242) included UBB, RN7SL1 (SEQ ID NO:229), RN7SK (SEQ ID NO:230), RPPH1, (SEQ ID NO:233), RMRP (SEQ ID NO:234), RNU2-2P (SEQ ID NO:235), SNORD3A (SEQ ID NO:236), MT-CO1 (SEQ ID NO:237), MT-CO3 (SEQ ID NO:238), MT-CO2 (SEQ ID NO:239). MBP (SEQ ID NO:240), and SNAP25 (SEQ ID NO:241).

As seen from the results in Table 5 and FIG. 7, GAPDH (SEQ ID NO:242) transcripts were effectively depleted from the nucleic acid samples in a probe concentration dependent manner. Further, depletion of GAPDH (SEQ ID NO:242) had no observable depletion effect on any of the measured untargeted RNA transcripts including those listed in Table 1 (FIG. 8). In one aspect each of the three largest DNA probe to RNA ratio (i.e., 1000:1, 1.00:1, and 10:1) were effective for reducing the calculated FPKM for GAPDH (SEQ ID NO:242) by at least an order of magnitude relative to the undepleted control sample, with the 100:1 ratio exhibiting the greatest overall reduction in FPKM for GAPDH (SEQ ID NO:242). In another aspect a trend of decreasing depletion with decreasing DNA probe to RNA ratio was observed, with a notable reduction in depletion from sample 3 to sample 4, and from sample 4 to sample 5. Accordingly, it can be useful to tune the concentration of DNA probes used to target a particular RNA transcript in order to effectively deplete the target RNA transcript from a nucleic acid sample.

In a next experiment, selective depletion of at least ten of the most highly expressed transcripts from Human Brain Reference RNA (AMBION) was demonstrated. DNA probes were designed against fourteen target RNA transcripts (Tables 1 and 2), and a number of probe combinations were prepared as 5 μM or 10 μM stock solutions (Table 6). RNase H treatment, stranded RNA library preparation, PCR amplification, and sequencing were performed as described above for GAPDH (SEQ ID NO:242) depletion. In addition, rRNA was simultaneously targeted for depletion in all RNA samples.

TABLE 6

| Sample ID | DNA probes | Concentration (μM) |
|---|---|---|
| A | GAPDH (SEQ ID NO: 242) | 10 |
| B | MBP (SEQ ID NO: 240) | 10 |
| C | MT-CO1 (SEQ ID NO: 237), MT-CO2 (SEQ ID NO: 239), MT-CO3 (SEQ ID NO: 238) | 10 |
| D | RN7SL1 (SEQ ID NO: 229), RN7SK (SEQ ID NO: 230), RN7SL4P (SEQ ID NO: 231), RN7SL5P (SEQ ID NO: 232), RPPHI (SEQ ID NO: 233), RMRP (SEQ ID NO: 234), RNU2-2P (SEQ ID NO: 235) | 10 |
| E | SNORD3A (SEQ ID NO: 236), SNAP25 (SEQ ID NO: 241) | 10 |
| F | MBP (SEQ ID NO: 240), MT-CO1 (SEQ ID NO: 237), MT-CO2 (SEQ ID NO: 239), MT-CO3 (SEQ ID NO: 238), RN7SL1 (SEQ ID NO: 229), RN7SK (SEQ ID NO: 230), RN7SL4P (SEQ ID NO: 231); RN7SL5P (SEQ ID NO: 232), RPPHI (SEQ ID NO: 233), RMRP (SEQ ID NO: 234), RNU2-2P (SEQ ID NO: 235), SNORD3A (SEQ ID NO: 236), SNAP25 (SEQ ID NO: 241) | 5 |

Figure 9:
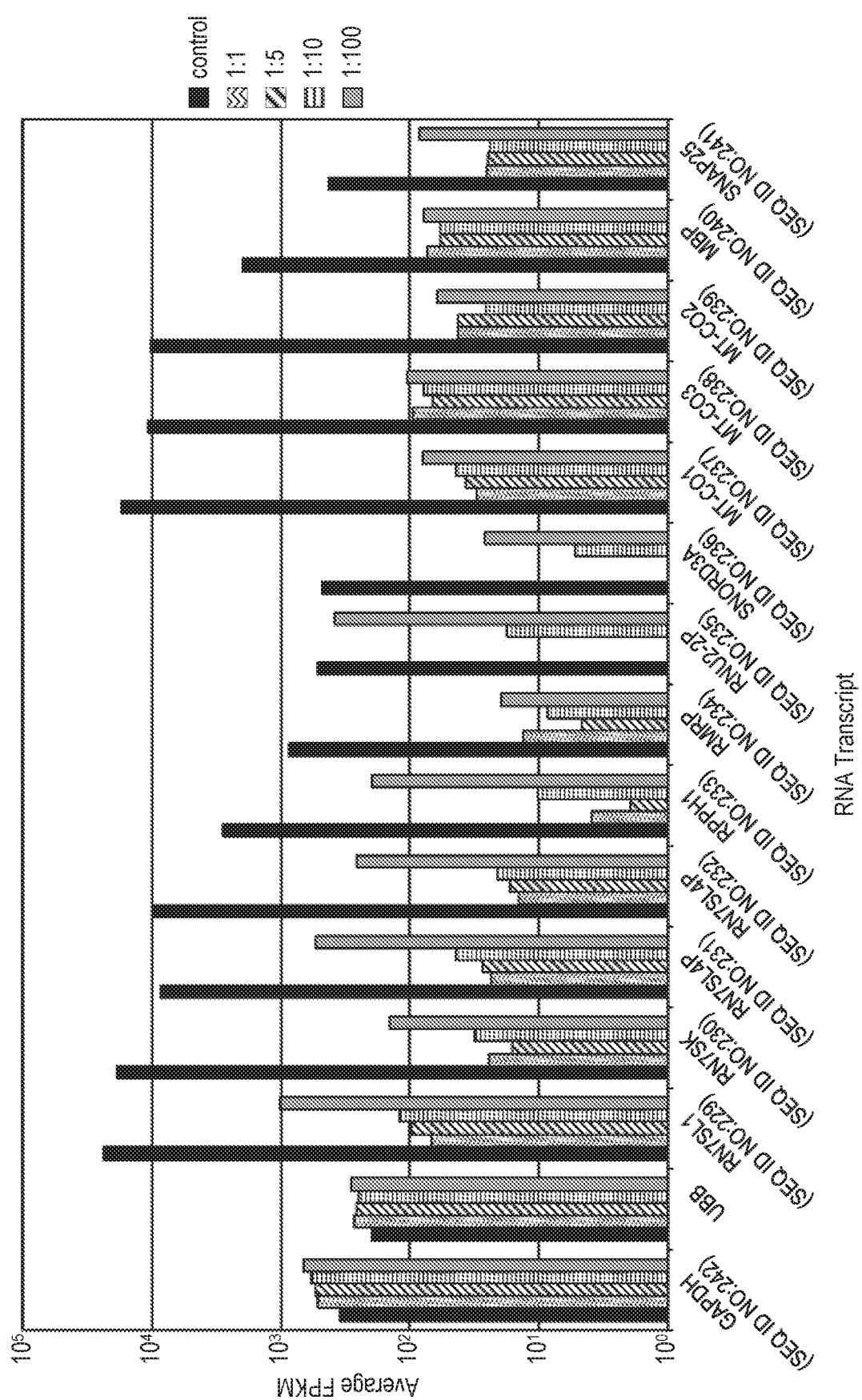
FIG. 9 is a plot of FPKM values for thirteen unique RNA transcripts targeted for depletion as a function of DNA probe to target RNA transcript ratio for five separate depletion experiments. DNA probes designed for depletion of thirteen unique RNA transcripts were added to total RNA samples at a DNA probe to target RNA transcript ratio of 1:1, 1:5, 1:10, or 1:100. Control data were collected for a total RNA sample with DNA probes targeting the thirteen unique RNA transcripts omitted (control). The effect of DNA probe to target RNA transcript ratio on measured FPKM following depletion and sequencing was compared against untargeted RNA transcripts including GAPDH (SEQ ID NO:242) and UBB. The thirteen unique target RNA transcripts included RN7SL1 (SEQ ID NO:229), RN7SK (SEQ ID NO:230), RN7SL4P (SEQ ID NO:231), RN7SLSP (SEQ ID NO:232), RPPH1 (SEQ ID NO:233), RMRP (SEQ ID NO:234), RNU2-2P (SEQ ID NO: 235), SNORD3A (SEQ ID NO:236), MT-CO1 (SEQ ID NO:237), MT-CO3 (SEQ ID NO:238), MT-CO2 (SEQ ID NO:239), MBP (SEQ ID NO:240), and SNAP25 (SEQ ID NO:241).

With Reference to Table 7 and FIG. 9, the results for DNA probe combination targeting the most highly expressed RNA transcripts illustrates that at least ten RNA transcripts can be effectively depleted from a nucleic acid sample by RNase H mediated degradation of target RNA transcripts. Notably, Table 7 summarizes data collected from seven separate experiments in the left-most column under the heading "Gene(s) Depleted". For example, one experiment (control) omitted probes for targeted depletion, another experiment included probes targeted for depletion of GAPDH (SEQ ID NO:242) only, another experiment included probes targeted for depletion of SNORD3A (SEQ ID NO:236) and SNAP25 (SEQ ID NO:241), and yet another experiment (top 10) included probes targeted for depletion of greater than ten of the most highly expressed RNA transcripts. It will be appreciated that this "top 10" experiment excluded probes targeting GAPDH (SEQ ID NO:242) for depletion,

TABLE 7

| Gene(s) Depleted | oligo:RNA (μM/μg) | GAPDH (SEQ ID NO: 242) | UBB | RN7SL1 SEQ ID NO: 229 | RN7SK SEQ ID NO: 230 | RN7SL4P (SEQ ID NO: 231) |
|---|---|---|---|---|---|---|
| control | n.a. | 351 | 195 | 23617 | 18584 | 8501 |
| GAPDH (SEQ ID NO: 242) | 2.2 | n.d. | 205 | 29986 | 22250 | 11275 |
|  | 0.22 | n.d. | 199 | 23594 | 19637 | 10092 |
| MBP (SEQ ID NO: 240) | 2.2 | 424 | 200 | 36394 | 12220 | 12526 |
|  | 0.22 | 423 | 226 | 35892 | 16831 | 13122 |

TABLE 7-continued

| Gene(s) Depleted | oligo:RNA (μM/μg) | | | | | |
|---|---|---|---|---|---|---|
| MT-CO* (SEQ ID NOs: 237-239) | 2.2 | 447 | 205 | 41377 | 16529 | 11071 |
|  | 0.22 | 466 | 223 | 85049 | 26014 | 14547 |
| RN7S* (SEQ ID NOs: 229-232), RPPH1 (SEQ ID NO: 233), RMRP (SEQ ID NO: 234), RNU2-2P (SEQ ID NO: 235) | 22 | 575 | 311 | 78 | 22 | 25 |
|  | 2.2 | 551 | 241 | 161 | 45 | 57 |
|  | 0.22 | 604 | 274 | 288 | 43 | 152 |
| SNORD3A (SEQ ID NO: 236), SNAP25 (SEQ ID NO: 241) | 2.2 | 497 | 236 | 81060 | 26787 | 13724 |
|  | 0.22 | 643 | 336 | 135996 | 38730 | 25145 |
| top 10 | 11 | 519 | 269 | 68 | 24 | 23 |
|  | 1.1 | 542 | 259 | 96 | 16 | 27 |
|  | 0.11 | 576 | 247 | 120 | 31 | 44 |
|  | 0.011 | 670 | 288 | 1017 | 143 | 541 |

| Gene(s) Depleted | oligo:RNA (μM/μg) | RN7SL5P (SEQ ID NO: 232) | RPPH1 (SEQ ID NO: 233) | RMRP (SEQ ID NO: 234) | RNU2-2P (SEQ ID NO: 235) | SNORD3A (SEQ ID NO: 236) |
|---|---|---|---|---|---|---|
| control | n.a | 9917 | 2838 | 860 | 518 | 474 |
| GAPDH (SEQ ID NO: 242) | 2.2 | 11998 | 4640 | 1447 | 1254 | 870 |
|  | 0.22 | 11434 | 3553 | 1097 | 830 | 814 |
| MBP (SEQ ID NO: 240) | 2.2 | 13254 | 5286 | 2103 | 1859 | 1143 |
|  | 0.22 | 13631 | 5161 | 1957 | 1897 | 1449 |
| MT-CO* (SEQ ID NOs: 237-239) | 2.2 | 12481 | 5530 | 1740 | 1874 | 1268 |
|  | 0.22 | 18333 | 8358 | 2328 | 2976 | 4191 |
| RN7S* (SEQ ID NOs: 229-232), RPPH1 (SEQ ID NO: 233), RMRP (SEQ ID NO: 234), RNU2-2P (SEQ ID NO: 235) | 22 | 18 | n.d. | 5 | n.d. | 5655 |
|  | 2.2 | 31 | 4 | n.d. | 6 | 5222 |
|  | 0.22 | 51 | 31 | 11 | 133 | 4514 |
| SNORD3A (SEQ ID NO: 236), SNAP25 (SEQ ID NO: 241) | 2.2 | 16853 | 8194 | 2266 | 3353 | n.d. |
|  | 0.22 | 29599 | 14568 | 3013 | 1903 | 25 |
| top 10 | 11 | 14 | 4 | 13 | n.d. | n.d. |
|  | 1.1 | 17 | 2 | 5 | n.d. | n.d. |
|  | 0.11 | 21 | 10 | 9 | 18 | 5 |
|  | 0.011 | 261 | 195 | 20 | 383 | 26 |

| Gene(s) Depleted | oligo:RNA (μM/μg) | MT-CO1 (SEQ ID NO: 237) | MT-CO3 (SEQ ID NO: 238) | MT-CO2 (SEQ ID NO: 239) | MBP (SEQ ID NO: 240) | SNAP25 (SEQ ID NO: 241) |
|---|---|---|---|---|---|---|
| control | n.a | 17287 | 10665 | 10247 | 1971 | 423 |
| GAPDH (SEQ ID NO: 242) | 2.2 | 13154 | 8730 | 7376 | 1888 | 451 |
|  | 0.22 | 15855 | 10244 | 9257 | 1862 | 445 |
| MBP (SEQ ID NO: 240) | 2.2 | 12541 | 7632 | 6414 | 71 | 466 |
|  | 0.22 | 12128 | 8074 | 7027 | 73 | 463 |
| MT-CO* (SEQ ID NOs: 237-239) | 2.2 | 98 | 137 | 102 | 1989 | 469 |
|  | 0.22 | 52 | 83 | 56 | 2109 | 441 |
| RN7S* (SEQ ID NO: 229-232), RPPH1 (SEQ ID NO: 233), RMRP (SEQ ID NO: 234), RNU2-2P (SEQ ID NO: 235) | 22 | 11043 | 6293 | 5971 | 2333 | 492 |
|  | 2.2 | 10962 | 6297 | 5814 | 2249 | 479 |
|  | 0.22 | 10817 | 6560 | 5589 | 2190 | 495 |
| SNORD3A (SEQ ID NO: 236), SNAP25 (SEQ ID NO: 241) | 2.2 | 9487 | 5952 | 5027 | 1948 | 35 |
|  | 0.22 | 8593 | 5256 | 4585 | 3016 | 72 |
| top 10 | 11 | 30 | 95 | 42 | 73 | 25 |
|  | 1.1 | 37 | 66 | 42 | 58 | 25 |
|  | 0.11 | 44 | 79 | 26 | 58 | 24 |
|  | 0.011 | 79 | 105 | 62 | 78 | 83 |

The thirteen target RNA transcripts selected for depletion in the data illustrated in the last row of Table 7 (top 10) and in FIG. 9 included RN7SL1 (SEQ ID NO:229), RN7SK (SEQ ID NO:230), RN7SL4P (SEQ ID NO:231). RN7SLSP (SEQ ID NO:232), RPPH1 (SEQ ID NO:233), RMRP (SEQ ID NO:234), RUN2-2P (SEQ ID NO: 235), SNORD3A (SEQ ID NO:236), MT-CO1 (SEQ ID NO:237). MT-CO3 (SEQ ID NO:238), MT-CO2, MBP (SEQ ID NO:240), and SNAP25S (SEQ ID NO:241). Notably, GAPDH (SEQ ID NO:242) was not targeted for depletion. Each of the target RNA transcripts were depleted for each of the DNA probe to target RNA transcript ratios tested as compared with the undepleted control sample where no DNA probes were used. In one aspect, the DNA probe to target RNA transcript ratio resulting in the greatest reduction in FPKM varied for each of the target RNA transcripts. For example, a ratio of 1:1 resulted in the greatest reduction for target RNA transcripts including RN7SL1 (SEQ ID NO:229) and MT-CO1 (SEQ ID NO:237), a ratio of 1:5 resulted in the greatest reduction for target RNA transcripts including RN7SK (SEQ ID NO:230) and RPPH1 (SEQ ID NO:233), and a ratio of 1:1.0 resulted in the greatest reduction for target RNA transcripts including MT-CO2 (SEQ ID NO:239) and SNAP25 (SEQ ID NO:241.). Accordingly, as an alternative to selecting a fixed DNA probe ratio for each target RNA transcript, it can be useful to select a different DNA probe ratio for each unique target RNA transcript Note that is Table 7, under the heading, "Gene(s) Depleted", MT-CO* Includes target RNA transcripts MT-CO1 (SEQ ID NO:237), MT-CO2 (SEQ ID NO:239), and MT-CO3 (SEQ ID NO:238). Similarly, RN7S* Includes target RNA transcripts RN7SL1. (SEQ ID NO:229), RN7SL4P (SEQ ID NO:231), RN7SLSP (SEQ ID NO:232), and RN7SK (SEQ ID NO:230).

With continued reference to FIG. 9 and Table 7, depletion of the target RNA transcripts was not observed to have a deleterious effect on untargeted RNA transcripts including GAPDH (SEQ ID NO:242) and UBB. By contrast, the observation was made that the average FPKM for GAPDH (SEQ ID NO:242) and UBB generally increased for depleted samples relative to the control sample. In one aspect, an increase in FPKM for untargeted RNA transcripts might be anticipated as the total number of reads for the selected sequencing method is generally a fixed number. By depleting target RNA transcripts, fewer sequencing reads are consumed by the target RNA transcripts, thereby making a greater number or sequencing reads available for consumption by untargeted RNA transcripts. Therefore, embodiments of the present disclosure anticipate methods of increasing the detectability of low abundance RNA transcripts through targeted depletion of comparatively high abundance transcripts, medium abundance transcripts, or a combination thereof.

Another outcome of depleting highly expressed transcripts was an increase in the efficiency of RNA-seq experiments and the sensitivity for detecting more lowly expressed transcripts in an RNA sample. To measure the effect of depleting highly expressed transcripts on the detection of lowly expressed transcripts by sequencing the above data (FIG. 9, Table 7) was analyzed in order to identify changes in the rank order (from high to low, according to FPKM quantification) for the thirteen targeted RNA transcripts listed in the last row (top 10) of Table 7 with and without depletion. Notably, GAPDH (SEQ ID NO:242) was not targeted for depletion in this experiment. However, the RNA transcript RN7SL2 (NR_127260.1) (SEQ ID NO:243), which was determined to have greater than 99% sequence identity with RN7SL1 (SEQ ID NO:229), was additionally targeted for depletion, thereby bringing the total number of targeted RNA transcripts to fourteen.

With reference to Table 8, the observation was made that the rank order (FPKM, high to low) of genes whose RNA transcripts were targeted for depletion decreased significantly with depletion as compared to the control experiment without depletion.

TABLE 8

| Gene | undepleted | | depleted | | |
|---|---|---|---|---|---|
| | Rank | FPKM | Rank | FPKM | Depletion (%) |
| RN7SL2 (SEQ ID NO: 243) | 1 | 25,166 | 189 | 129 | 99.49 |
| RN7SL1 (SEQ ID NO: 229) | 2 | 23,617 | 506 | 68 | 99.71 |
| RN7SK (SEQ ID NO: 230) | 3 | 18,584 | 2,200 | 24 | 99.87 |
| MT-CO1 (SEQ ID NO: 237) | 4 | 17,287 | 1,600 | 30 | 99.82 |
| MT-CO3 (SEQ ID NO: 238) | 8 | 10,665 | 308 | 95 | 99.11 |
| MT-CO2 (SEQ ID NO: 239) | 10 | 10,247 | 1,002 | 42 | 99.59 |
| RN7SL5P (SEQ ID NO: 232) | 11 | 9,917 | 4,240 | 14 | 99.86 |
| RN7SL4P (SEQ ID NO: 231) | 12 | 8,501 | 2,367 | 23 | 99.73 |
| RPPH1 (SEQ ID NO: 233) | 20 | 2,838 | n.a. | <5 | >99 |
| MBP (SEQ ID NO: 240) | 22 | 1,971 | 461 | 73 | 96.30 |
| RMRP (SEQ ID NO: 234) | 28 | 860 | 4,615 | 13 | 98.47 |
| RNU2-2P (SEQ ID NO: 235) | 35 | 518 | n.a. | <5 | >99 |
| SNORD3A (SEQ ID NO: 236) | 36 | 474 | n.a. | <5 | >99 |
| SNAP25 (SEQ ID NO: 241) | 38 | 423 | 2,105 | 25 | 94.03 |

The concept that the depletion of highly expressed transcripts facilitates detection of more lowly expressed transcripts in an RNA-seq experiment was supported by the observation that the control experiment (no depletion) had 8,521 unique transcripts that were ranked with values greater than 5 FPKM, with the average transcript detected at 48.26 FPKM. By comparison, the experimental data (with depletion of the fourteen target genes) had 9,561 unique transcripts that were ranked with values greater than 5 FPKM, with the average transcript detected at 27.41 FPKM. Accordingly, depletion of the fourteen target RNA transcripts enabled the detection of 1,040 additional genes with at least 5 FPKM that would not have been otherwise detected, which corresponded to an increase in the number of unique RNA transcripts detected of 12%. A selection of genes from the list of 1,040 genes that were otherwise undetectable without depletion (within the detection threshold of the experiment), and which are known to be involved in human disease, are listed in Table 9.

TABLE 9

| Gene | Phenotype (MIM Number) |
|---|---|
| COX15 | Cardioencephalomyopathy, Fatal Infantile (603646) |
| RARS2 | Pontocerebellar Hypoplasia, Type 6 (611524) |
| CA4 | Retinitis Pigmentosa 17 (114760) |
| AASS | Hyperlysinemia, Type 1 (605113) |
| DNASE1 | Systemic Lupus Erythematosus, Susceptibility To (125505) |
| MUTYH | Familial Adenomatous Polyposis 2 (604933) |
| DOCK8 | Hyper-IgE Recurrent Infection Syndrome, Recessive (611432) |
| ATR | Seckel Syndrome 1 (601215) |
| GLE1 | Lethal Congenital Contracture Syndrome 1 (603371) |
| KIF22 | Spondyloepimetaphyseal Dysplasia with Joint Laxity, Type 2 (603213) |
| MCM9 | Ovarian Dysgenesis 4 (610098) |
| RECQL4 | Rothmund-Thomson Syndrome (603780) |
| MMP14 | Winchester Syndrome (600754) |
| CLN8 | Ceroid Lipofuscinosis, Neuronal, 8 (607837) |
| kDM6A | Kabuki Syndrome 2 (300128) |
| CDk6 | Microcephaly 12, Primary, Autosomal Recessive (603368) |
| CTSC | Papillon-Lefevre Syndrome (602365) |
| FBXL4 | Mito DNA Depletion Synd 13 (Encephalomyopathic Type) (605654) |
| TPMT | Thiopurine S-Methyltransferase Deficiency (187680) |

With reference to Table 9, the phenotype of each of the listed genes along with the associated Mendelian Inheritance in Man (MIM) number was determined using the Online Mendelian inheritance in Man (OMIM) database. In one aspect, many genes involved in human disease or phenotypic variation when mutated are expressed at low levels. Thus, the data illustrated that embodiments of the present disclosure can be used to increase the sensitivity of experiments or tests that depend on the relative abundances of transcripts in RNA samples.

The schematic flow charts shown in the Figures are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed in the Figures are provided to explain the logical steps of the method and are understood not to limit the scope of the method. Although various arrow types and line types may be employed, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention is presented in several varying embodiments in the following description with reference to the Figures, in which like numbers represent the same or similar elements. Reference throughout this specification to "one embodiment," "an embodiment." or similar language means that a particular feature, structure, or characteristic described in connection with the embodiment is included in at least one embodiment of the present invention. Thus, appearances of the phrases "in one embodiment." "in an embodiment" and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the system. One skilled in the relevant art will recognize, however, that the system and method may both be practiced without one or more of the specific details, or with other methods, components, materials, and so forth. In other instances, well-known structures, materials, or operations are not shown or described in detail to avoid obscuring aspects of the invention. Accordingly, the foregoing description is meant to be exemplary, and does not limit the scope of present inventive concepts.

Each reference identified in the present application is herein incorporated by reference in its entirety.

What is claimed is:

1. A method for depleting target nucleic acids from a nucleic acid sample, the method comprising:
   hybridizing a plurality of deoxyribonucleic acid (DNA) probes with a plurality of target ribonucleic acid (RNA) transcripts in the nucleic acid sample, wherein one or more of the plurality of DNA probes forms one or more heteroduplexes with one or more of the plurality of target RNA transcripts, wherein the DNA probes are hybridizable along the length of each of the target RNA transcripts with a regular spacing; and
   treating the one or more heteroduplexes with one or more enzymes having RNA-DNA hybrid ribonucleotidohydrolase activity, thereby degrading at least the RNA portion of the one or more heteroduplexes.

2. The method of claim 1, wherein the plurality of DNA probes hybridizes to at least 3 unique target RNA transcripts.

3. The method of claim 1, wherein the plurality of DNA probes comprises at least 100 unique DNA probes.

4. The method of claim 1, wherein the fraction of the total number of bases of each target RNA transcript hybridizable by the DNA probes is at least 0.5.

5. The method of claim 4, wherein the fraction of the total number of bases of each target RNA transcript hybridizable by the DNA probes is at least 0.75.

6. The method of claim 5, wherein the fraction of the total number of bases of each target RNA transcript hybridizable by the DNA probes is at least 0.9.

7. The method of claim 1, wherein the plurality of DNA probes hybridizes to at least 10 unique target RNA transcripts.

8. The method of claim 7, wherein the plurality of DNA probes hybridizes to at least 100 unique target RNA transcripts.

9. The method of claim 1, wherein the regular spacing is less than about 50 bases.

10. The method of claim 9, wherein the regular spacing is less than about 10 bases.

11. The method of claim 1, wherein the quantity of the target RNA transcript is depleted by at least about 50%.

12. The method of claim 11, wherein the quantity of the target RNA transcripts is depleted by at least about 80%.

13. A method for depleting target nucleic acids from a nucleic acid sample, the method comprising:
   selecting a plurality of target ribonucleic acid (RNA) transcripts to deplete from a nucleic acid sample, each of the target RNA transcripts derived from a corresponding deoxyribonucleic acid (DNA) having a known sequence;
   designing a plurality of DNA probes to hybridize along the length of the target RNA transcripts with a regular spacing;
   synthesizing the plurality of DNA probes hybridizable to form a heteroduplex with at least one of the plurality of target RNA transcripts;
   hybridizing the plurality of DNA probes with the target RNA transcripts in the nucleic acid sample, each of the DNA probes forming a heteroduplex with at least one of the plurality of target RNA transcripts; and
   treating the heteroduplex with an enzyme having RNA-DNA hybrid ribonucleotidohydrolase activity, thereby degrading at least the RNA portion of the heteroduplex, and
   wherein the plurality of DNA probes hybridizes to at least 3 unique target RNA transcripts.

14. The method of claim 13, wherein the regular spacing is less than about 50 bases.

* * * * *